United States Patent [19]

Sakashita et al.

[11] Patent Number: 5,480,580
[45] Date of Patent: Jan. 2, 1996

[54] OPTICALLY ACTIVE COMPOUND HAVING A δ-VALEROLACTONE RING AND LIQUID CRYSTAL COMPOSITION CONTAINING SAME

[75] Inventors: Keiichi Sakashita, Otake; Yoshitaka Kageyama; Tetsuya Ikemoto, both of Kawsaki, all of Japan

[73] Assignee: Mitsubishi Rayon Company Ltd., Japan

[21] Appl. No.: 376,307

[22] Filed: Jan. 23, 1995

Related U.S. Application Data

[63] Continuation of Ser. No. 263,215, Jun. 17, 1994, abandoned, which is a continuation of Ser. No. 732,756, Jul. 19, 1991, abandoned.

[30] Foreign Application Priority Data

Jul. 20, 1990 [JP] Japan .................................. 2-192015
Oct. 3, 1990 [JP] Japan .................................. 2-265807

[51] Int. Cl.⁶ .................................................. C09K 19/34
[52] U.S. Cl. .................. 252/299.61; 549/273; 549/292; 546/268; 544/238; 544/298; 544/315; 544/334; 544/335; 544/336; 544/406; 544/408; 544/409
[58] Field of Search .................. 252/299.01, 299.61; 549/273, 292; 546/268; 544/238, 298, 315, 334, 335, 336, 406, 408, 409

[56] References Cited

U.S. PATENT DOCUMENTS

| | | | |
|---|---|---|---|
| 4,818,431 | 4/1989 | Eidenschink et al. | 252/299.61 |
| 4,909,957 | 3/1990 | Sakaguchi et al. | 252/299.61 |
| 5,026,506 | 6/1991 | Koden et al. | 252/299.61 |
| 5,045,228 | 9/1991 | Nakauchi et al. | 252/299.61 |
| 5,061,398 | 10/1991 | Takehara et al. | 252/299.61 |
| 5,124,069 | 6/1992 | Nakauchi et al. | 252/299.61 |
| 5,149,462 | 9/1992 | Sakashita et al. | 252/299.61 |
| 5,151,214 | 9/1992 | Koden et al. | 252/299.61 |
| 5,164,113 | 11/1992 | Ikemoto et al. | 252/299.61 |

FOREIGN PATENT DOCUMENTS

| | | |
|---|---|---|
| 0313379 | 4/1989 | European Pat. Off. . |
| 0388225 | 9/1990 | European Pat. Off. . |

OTHER PUBLICATIONS

Ferroelectric Liquid Crystals, J. Physique 36, L–69 (1975), R. B. Meyer et al.
J. Am. Chem. Soc., 103, 2151 (1981), T. Philip et al.
Synthesis of the Dideoxynucleosides ddC and CNT from Glutamic Acid, Ribonolactone, and Pyrimidine Bases, J. Org. Chem., 53, 4780–4786 (1988), D. L. Coffen et al.

*Primary Examiner*—Philip Tucker
*Attorney, Agent, or Firm*—Finnegan, Henderson, Farabow, Garrett & Dunner

[57] ABSTRACT

Optical active compounds which are chemically stable, are not colored, have a good optical stability, and which give a liquid crystal composition having a large spontaneous polarization when the compound is incorporated, are provided. The optical active compound have an asymmetric carbon atom fixed by a δ-valerolactone ring and the permanent dipole moment derived from the carboxylic group is fixed by the δ-valerolactone ring and two alkyl groups which can be regarded as a part of a measogen.

6 Claims, No Drawings

OPTICALLY ACTIVE COMPOUND HAVING A δ-VALEROLACTONE RING AND LIQUID CRYSTAL COMPOSITION CONTAINING SAME

This application is a continuation of application Ser. No. 08/263,215, filed Jun. 17, 1994, now abandoned, which is a continuation of application Ser. No. 07/732,756, filed Jul. 19, 1991, now abandoned.

BACKGROUND OF THE INVENTION

1. Field of the Invention

The present invention relates to a novel optically active compound having a δ-valerolactone ring in the structure thereof, and a liquid crystal composition comprising the same.

2. Description of the Related Art

Liquid crystals currently used in a liquid crystal display are classified into the nematic phase, and since they are of the light-receiving type, are featured by a freedom from eye fatigue and a very small power consumption. Nevertheless, these liquid crystals have problems such as a low response speed and an impossibility of viewing the display depending upon the viewing angle.

Display devices and printer heads using a ferroelectric liquid crystal having advantageous characteristics similar to those of the nematic liquid crystal, such as the property of not causing eye fatigue and a small power consumption, and having a high response speed and high contrast characteristics comparable to those of a light-emitting type display element, have been studied.

The ferroelectric liquid crystal was reported of its existence for the first time by R. B. Meyer et al. in 1975 [J. Physique, 36, L-69 (1975)]. This ferroelectric liquid crystal has a chiral smectic C phase (hereinafter referred to as "Sm*C phase"), and a typical example of the ferroelectric liquid crystal is p-decyloxybenzylidene-p'-amino-2-methylbutyl cinnamate (hereinafter referred to as "DOBAMBC") represented by the formula:

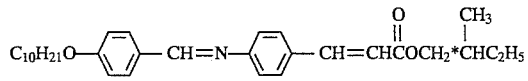

In the above-described DOBAMBC and most of the ferroelectric liquid crystals proposed thereafter, however, the range of temperature showing the ferroelectric property (the range of temperatures wherein the Sm*C phase is present) is very narrow, and these liquid crystal materials cannot be practically used alone. Therefore, attempts have been made to expand the range of temperatures showing the Sm*C phase to the lower and higher temperature sides, taking room temperature as the center, by mixing a variety of ferroelectric liquid crystals. A ferroelectric liquid crystal having a larger spontaneous polarization than heretofore proposed ferroelectric liquid crystals is desired for a printer head for which a very short response time is required.

An object of the present invention is to provide an optically active compound which is chemically stable, is not colored and has a good optical stability and which gives a liquid crystals composition having a large spontaneous polarization when the optically active compound is incorporated in a liquid crystal composition, and a liquid crystal composition comprising the compound.

SUMMARY OF THE INVENTION

In one aspect of the present invention, there is provided an optically active compound having a δ-valerolactone ring, which is represented by the general formula (1):

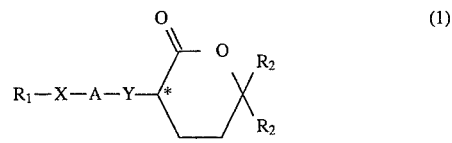

wherein $R_1$ represents a straight-chain or branched alkyl group having 1 to 18 carbon atoms, a straight-chain or branched alkenyl group having 2 to 18 carbon atoms, a straight-chain or branched alkoxyalkyl group having 1 to 3 carbon atoms in the alkoxy portion and 1 to 18 carbon atoms in the alkyl portion, or any of these groups with substituents wherein at least one hydrogen atom is substituted with a halogen, provided that when $R_1$ has a structure capable of having an optically active group, it may be an optically active group or a racemic modification; and two $R_2$'s which represent hydrogen atom or alkyl group having 1 to 18 carbon atoms. Examples of the alkyl group include a methyl group, an ethyl group, a propyl group, a butyl group, a hexyl group, an octyl group, a nonyl group, a decyl group and a dodecyl group. In the above-described formula, X represents a direct bond, —O—,

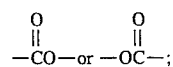

Y represents a direct bond,

—O—, —CH$_2$O— or —OCH$_2$—; A represents

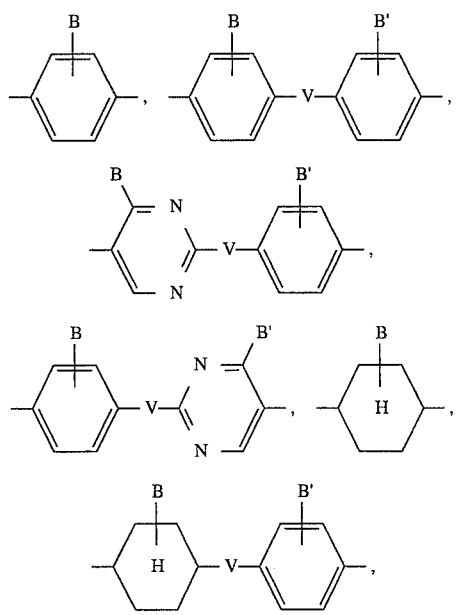

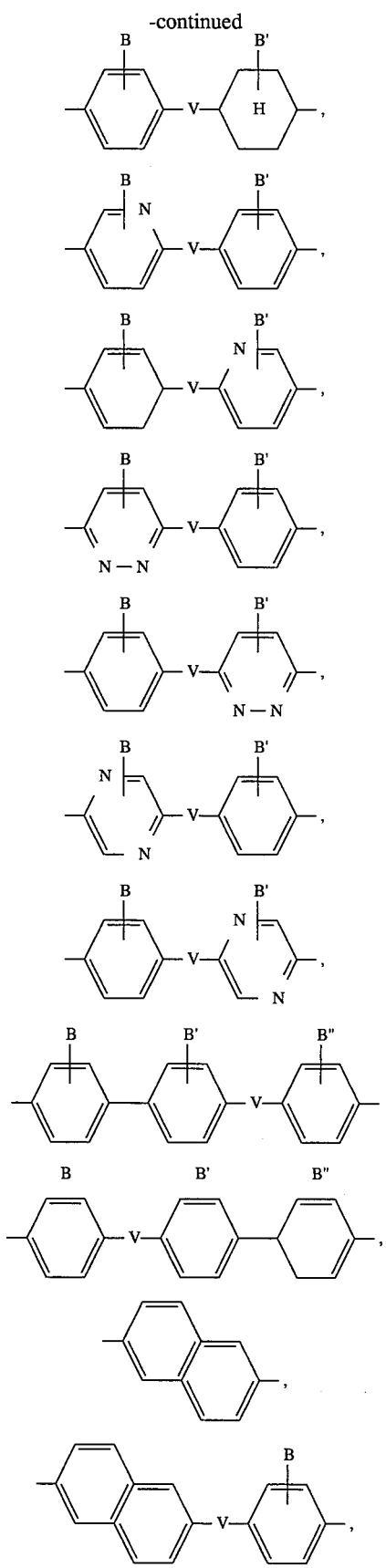

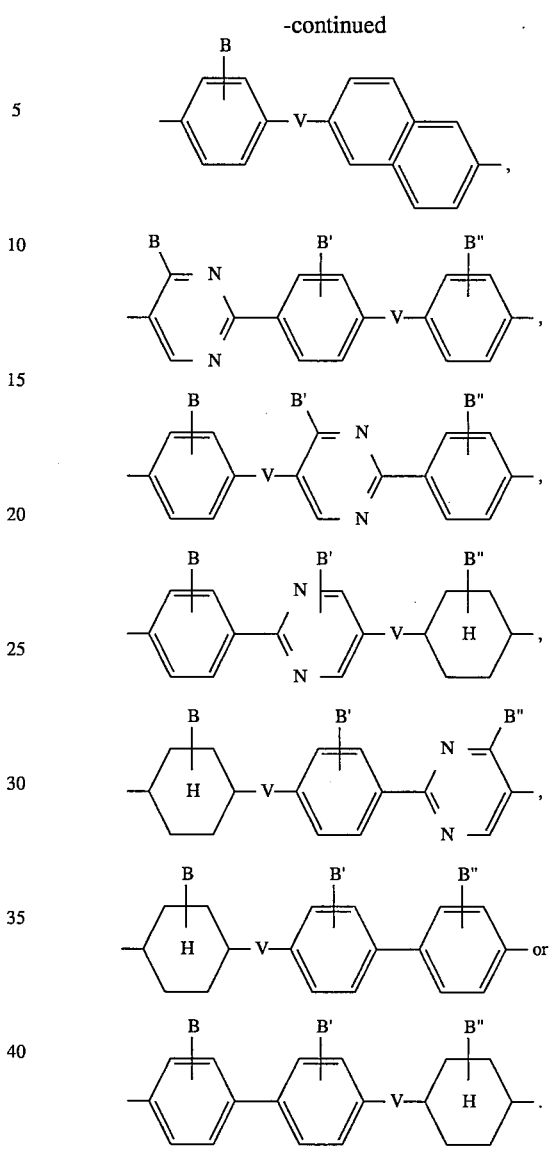

wherein B, B' and B" each independently represent a hydrogen atom, a halogen atom, a cyano group, a methyl group, a methoxy group or a trihalomethyl group and V represents a direct bond, —CH$_2$O—, —OCH$_2$—, $$-\overset{\overset{O}{\|}}{C}O- \text{ or } -O\overset{\overset{O}{\|}}{C}-;$$

and a carbon atom attached by * represents an asymmetric carbon atom.

In another aspect of the present invention, there is provided an optically active compound having a δ-valerolactone ring, which is represented by the general formula (2):

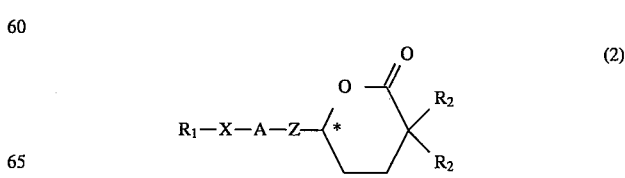

wherein $R_1$, X, A, $R_2$ and * are as defined above, Z represents a direct bond,

or $-OCH_2-$.

In a further aspect of the present invention, there is provided a liquid crystal composition comprising at least one member selected from the group consisting of optically active compounds having a δ-valerolactone ring represented by the general formulae (1) and (2).

In the optically active compound of the present invention, preferred examples of the $R_1$ in the general formula (1) include a straight-chain or branched alkyl group having 4 to 14 carbon atoms, a straight-chain or branched alkenyl group having 4 to 14 carbon atoms and a straight-chain or branched alkoxyalkyl group having 4 to 14 carbon atoms in the alkyl portion. Examples of the straight-chain alkyl group include n-butyl group, n-pentyl group, n-hexyl group, n-octyl group, n-nonyl group, n-decyl group, n-dodecyl group and n-tetradecyl group. Examples of the branched alkyl group include methyl-branched alkyl groups represented by the following formula:

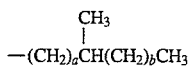

wherein a is an integer of from 0 to 10 and b is an integer of from 1 to 11, with the proviso that $1 \leq a+b \leq 11$.
These methyl-branched alkyl groups may be optically active groups or racemic modifications, and all of them are suitable for use in the present invention.

Preferred examples of the halogen-substituted alkyl group include groups represented by the following formula:

$$-(CH_2)_k CH(CH_2)_i CH_3$$
$$\quad\ \ |$$
$$\quad\ \ W$$

wherein W represents fluorine, chlorine or bromine atom, and k and i each independently represent an integer of from 0 to 12, with the proviso that $2 \leq k+i \leq 12$.
More preferably, it is a optically active group.

Examples of the halogen-substituted branched alkyl group include alkyl groups having a trifluoromethyl branch, and it is also more preferably an optically active group.

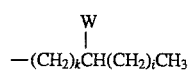

wherein a and b are as defined above.
Examples of the straight-chain alkoxyalkyl group include $-(CH_2)_c OC_j H_{2j+1}$, and examples of the branched alkoxyalkyl group include

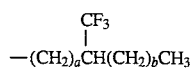

and

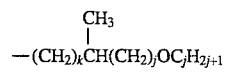

wherein j is an integer of from 1 to 3, c is an integer of from 4 to 14 and k and i are as defined above.
The branched alkoxyalkyl groups may be a racemic modification or optically active groups.

Preferred examples of A include

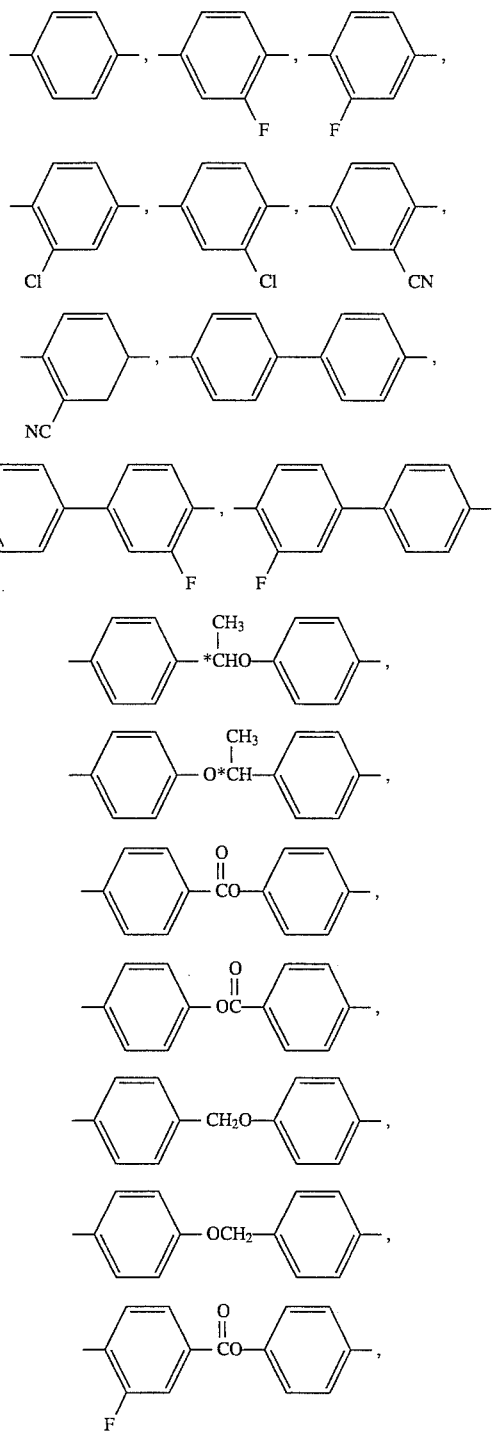

-continued

-continued
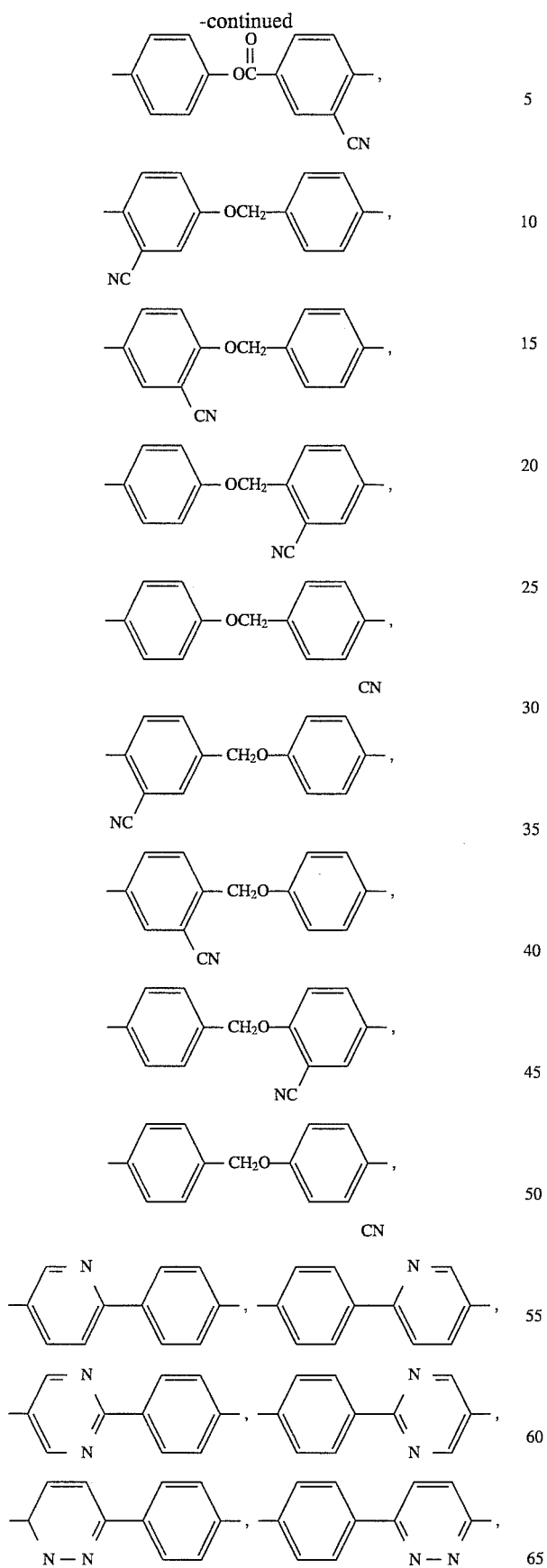
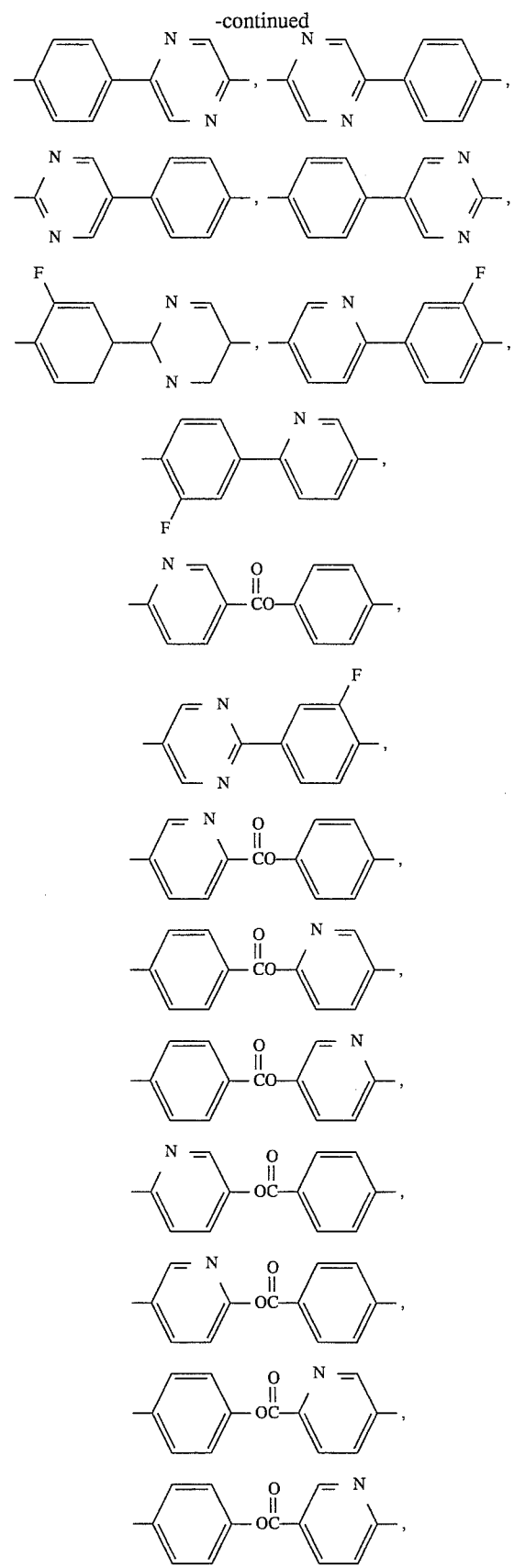

-continued
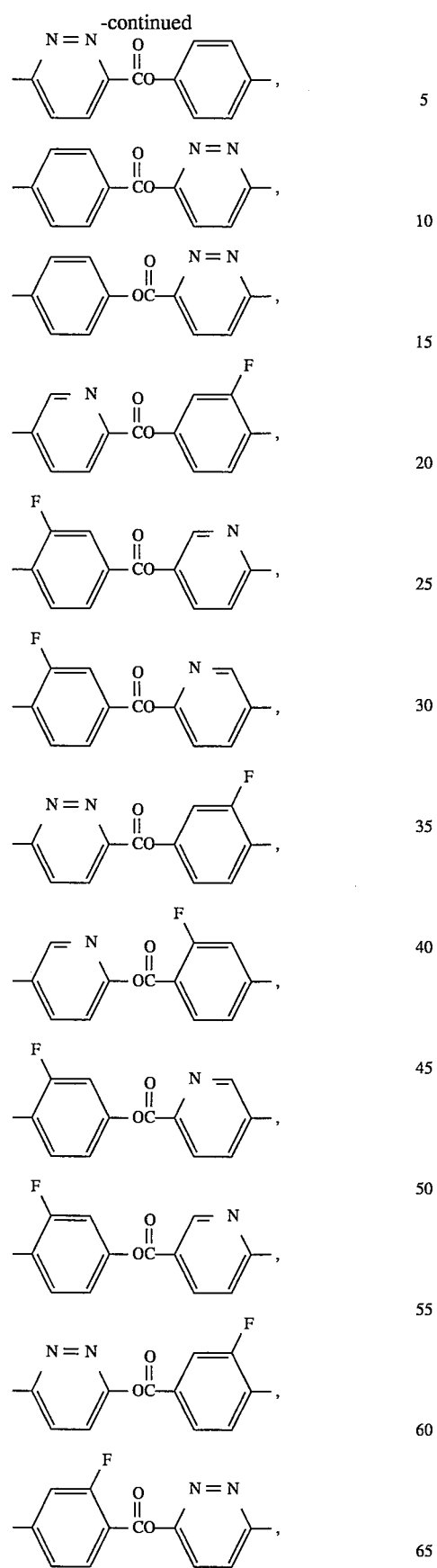
-continued
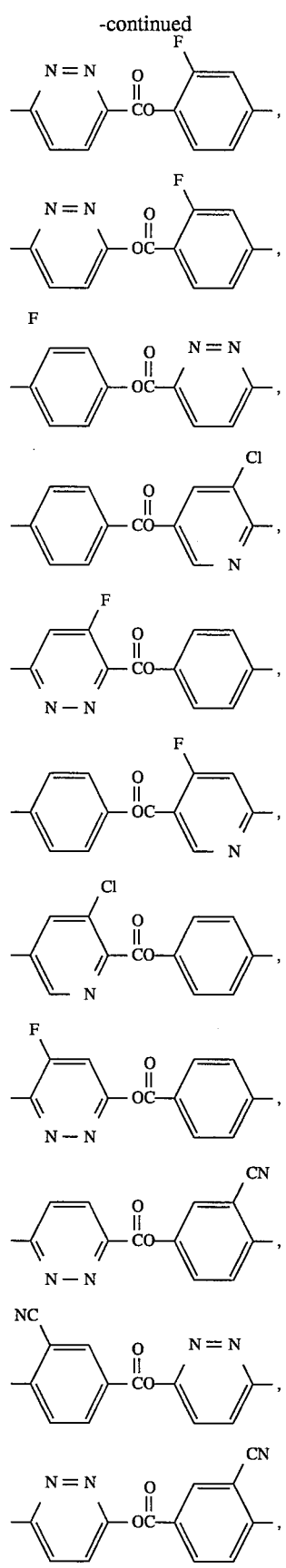

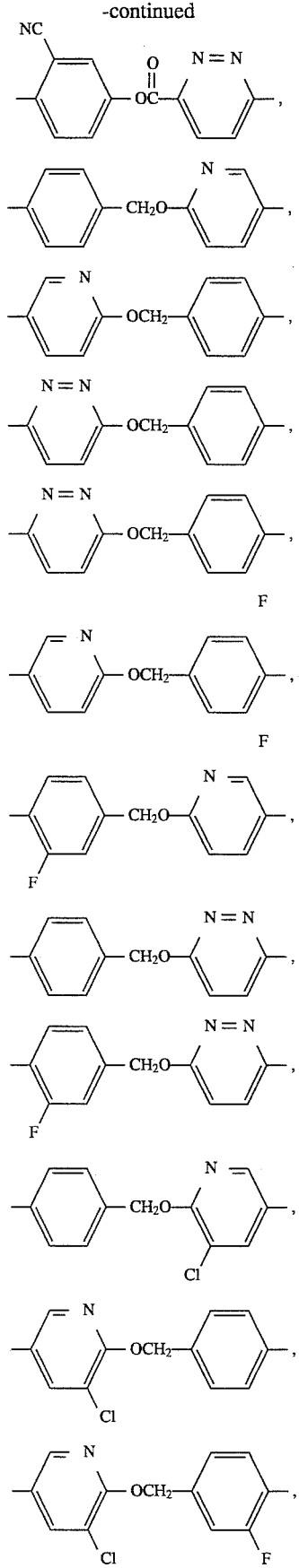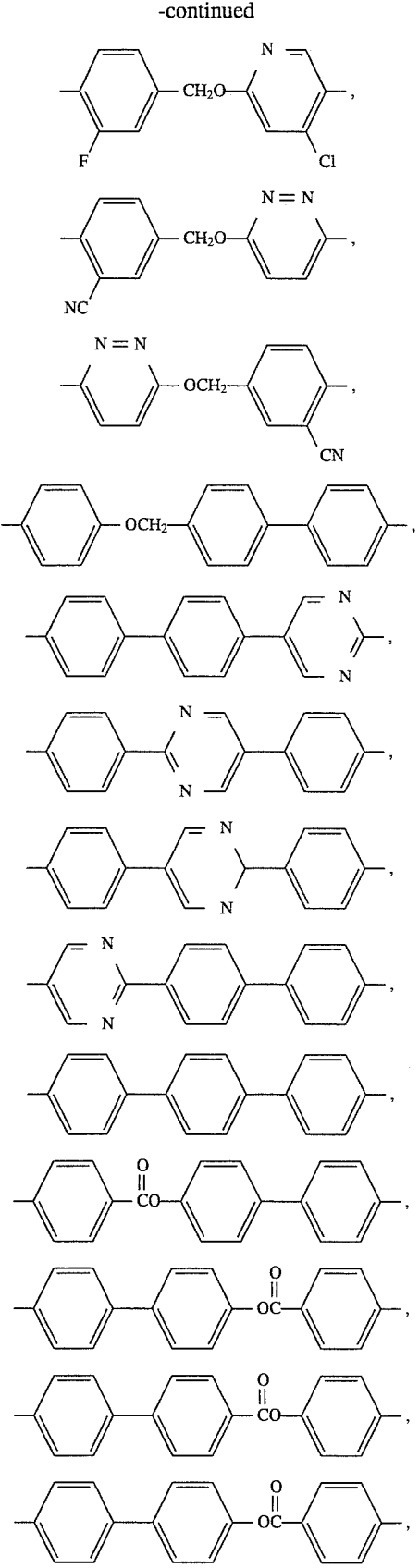

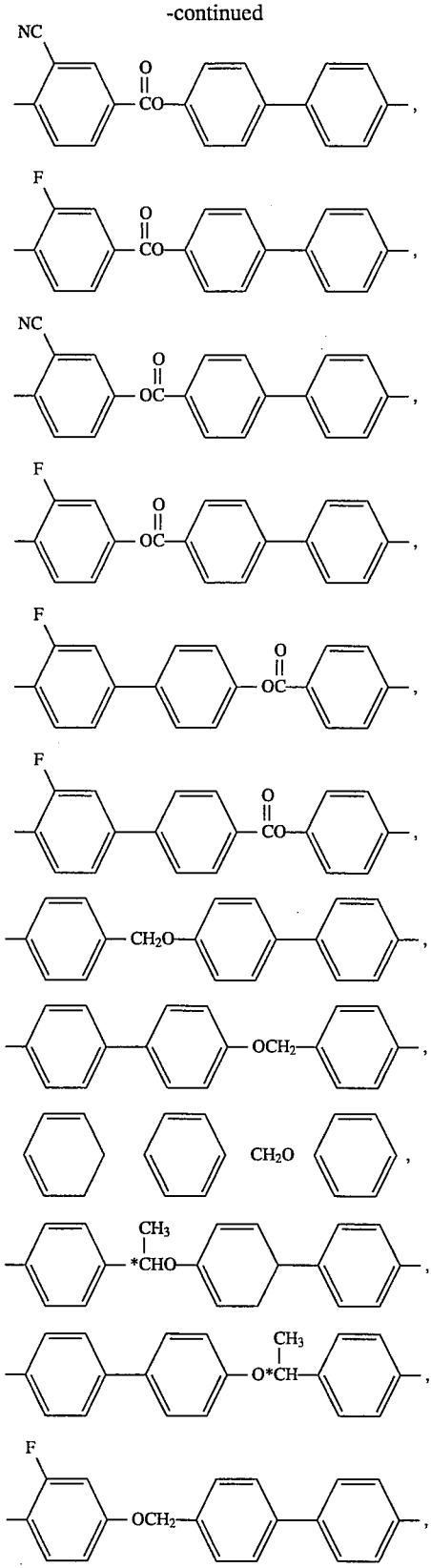
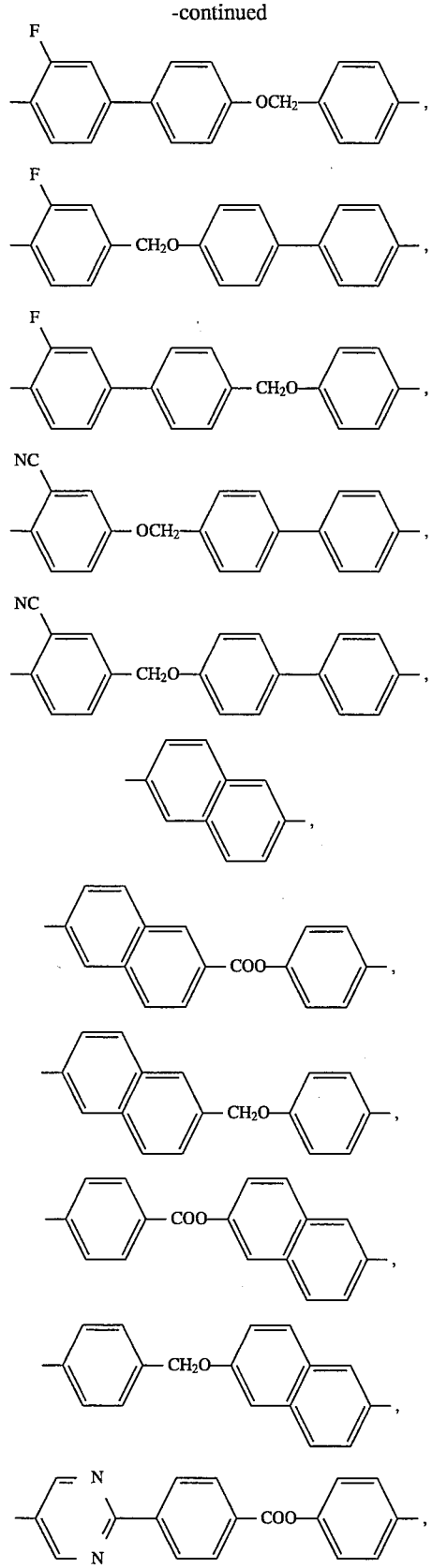

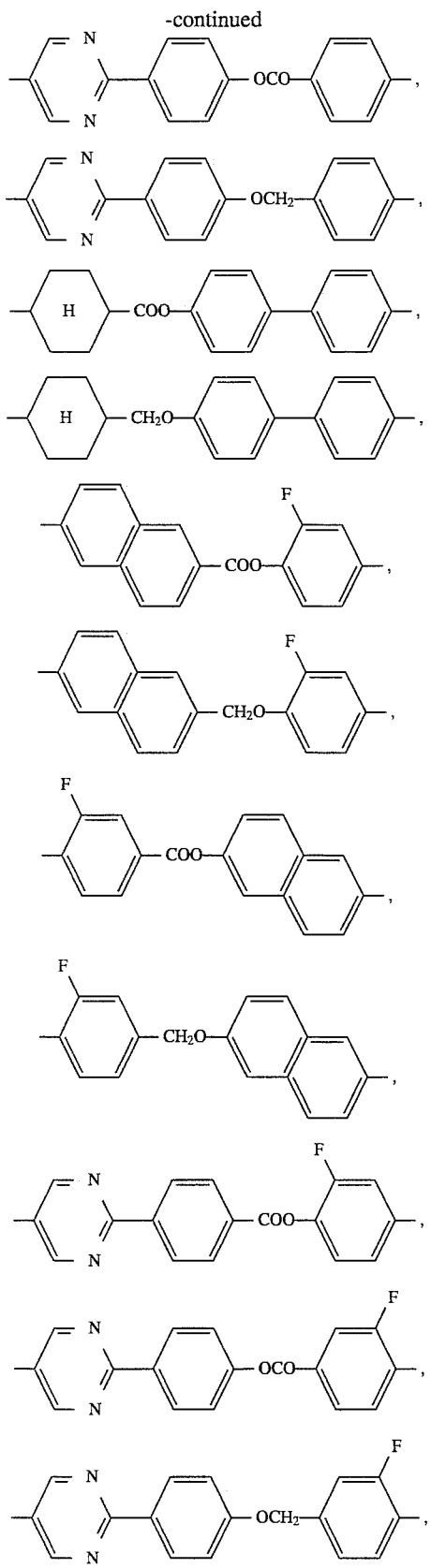

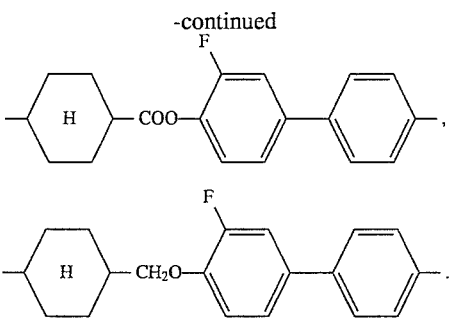

In a liquid crystal composition comprising the optically active compound of the present invention, an increase in the dipole moment around the asymmetric carbon atom or an increase in the rotational hindrance around the asymmetric carbon atom is preferred from the viewpoint of increasing the response speed. Accordingly, the Y in the general formula (1) is preferably a direct bond, —O— or

and the Z in the general formula (2) is preferably

or —OCH$_2$—. From the viewpoint of the linearity of the molecule and the ease of the appearance of the tilted liquid crystal phase by the induced dipole moment, the Y is preferably

—O—, —OCH$_2$— or —CH$_2$O—, and the Z is preferably —OCH$_2$—. From the viewpoint of the ease of the synthesis, the Y is preferably a direct bond, —CH$_2$O—, —O— or

and the Z is preferably a direct bond,

or —OCH$_2$—.

From the viewpoint of the ease of the synthesis, the X is preferably a direct bond, —O—,

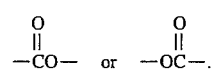

From the view point of the viscosity, the solubility will host mixtures, the V is preferably a direct bond, and from the viewpint of the magnitude of the dipole moment, the ease of the synthesis, etc., the V is preferably

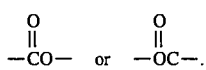

The compounds of the general formula (1) can be prepared according to the following processes.

Where Y is

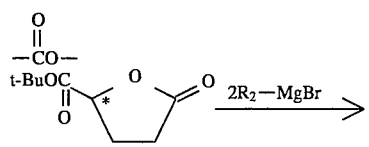

(3):

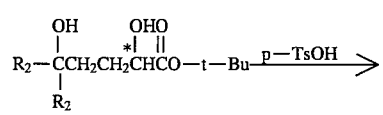

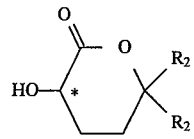

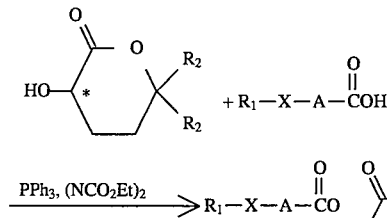

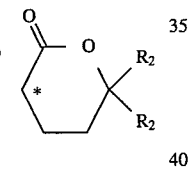

The compounds represented by the formula (3) can be synthesized also by the following process:

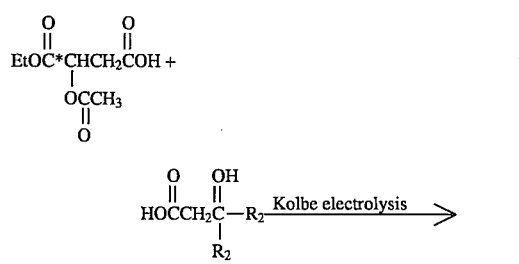

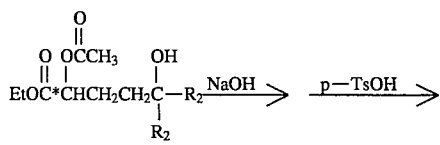

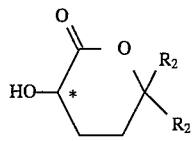

Where Y is —O—:

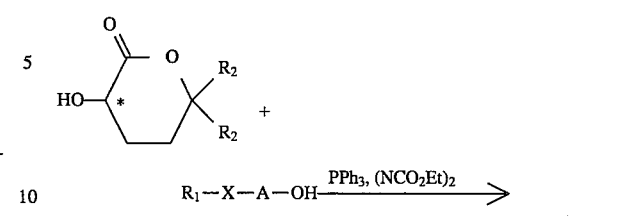

Where Y is —OCH$_2$—:

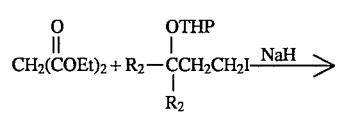

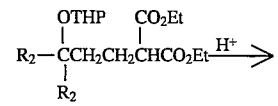

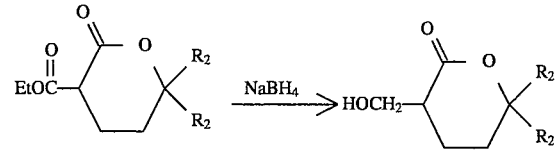

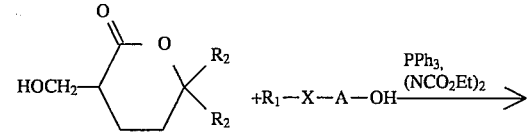

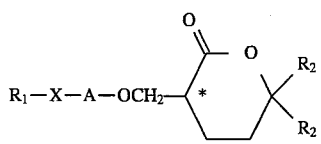

The compounds represented by the general formula (2) can be prepared by the following processes.

① Where Z is —OCH$_2$—:

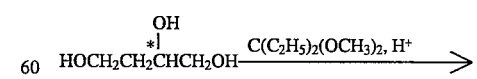

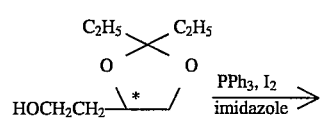

-continued
a) Where R$_2$'s are both an alkyl group:
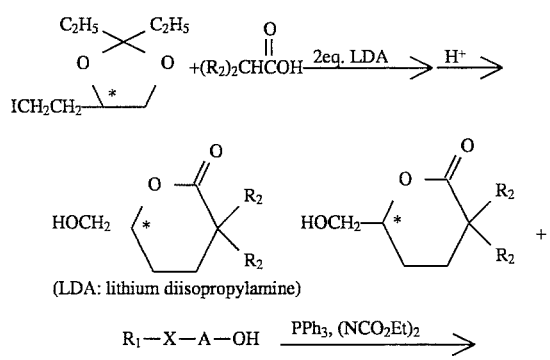
(LDA: lithium diisopropylamine)
b) Where R$_2$'s are both a hydrogen atom:
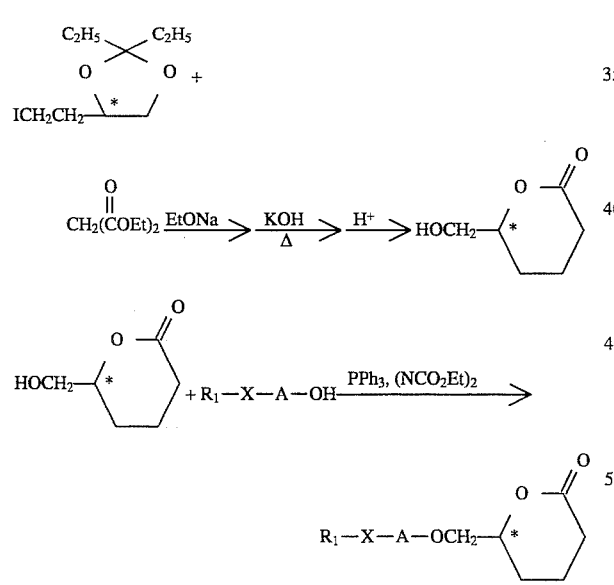
② Where Z is
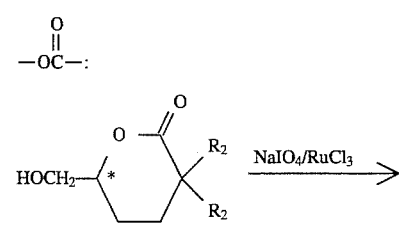
-continued
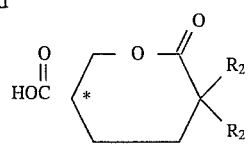
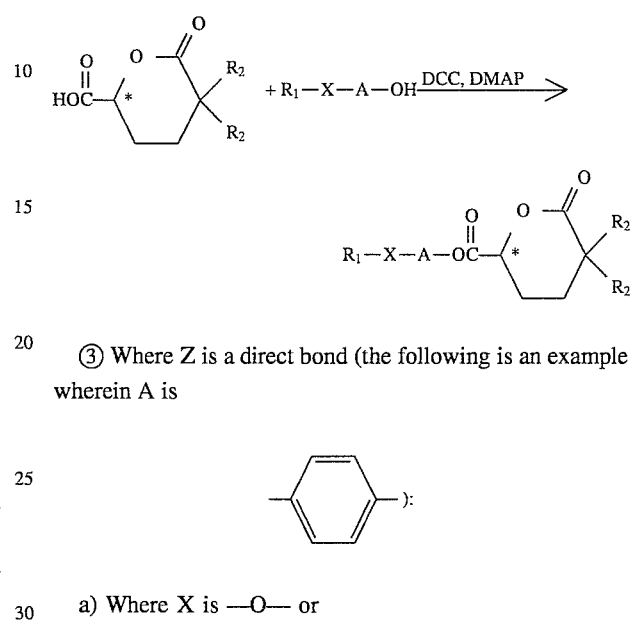
③ Where Z is a direct bond (the following is an example wherein A is
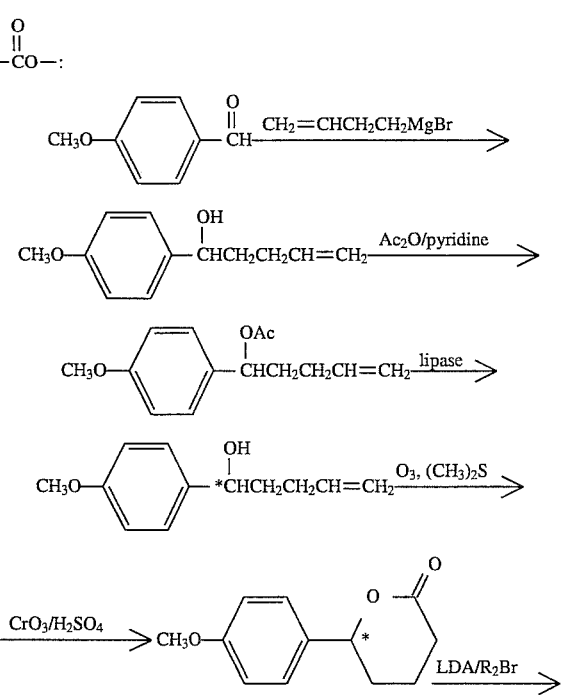 ):
a) Where X is —O— or
$$-\overset{O}{\underset{\|}{C}}O-:$$
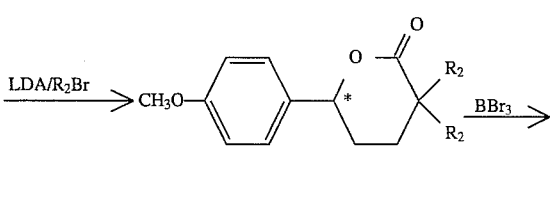

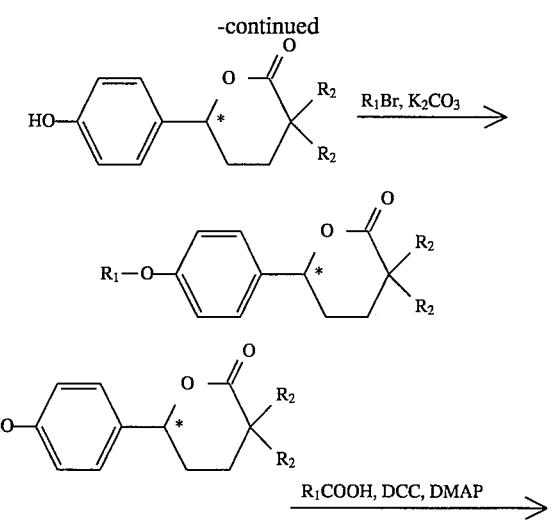
b) Where X is
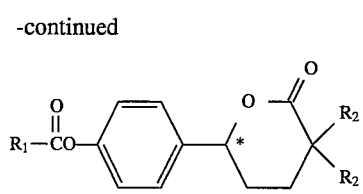
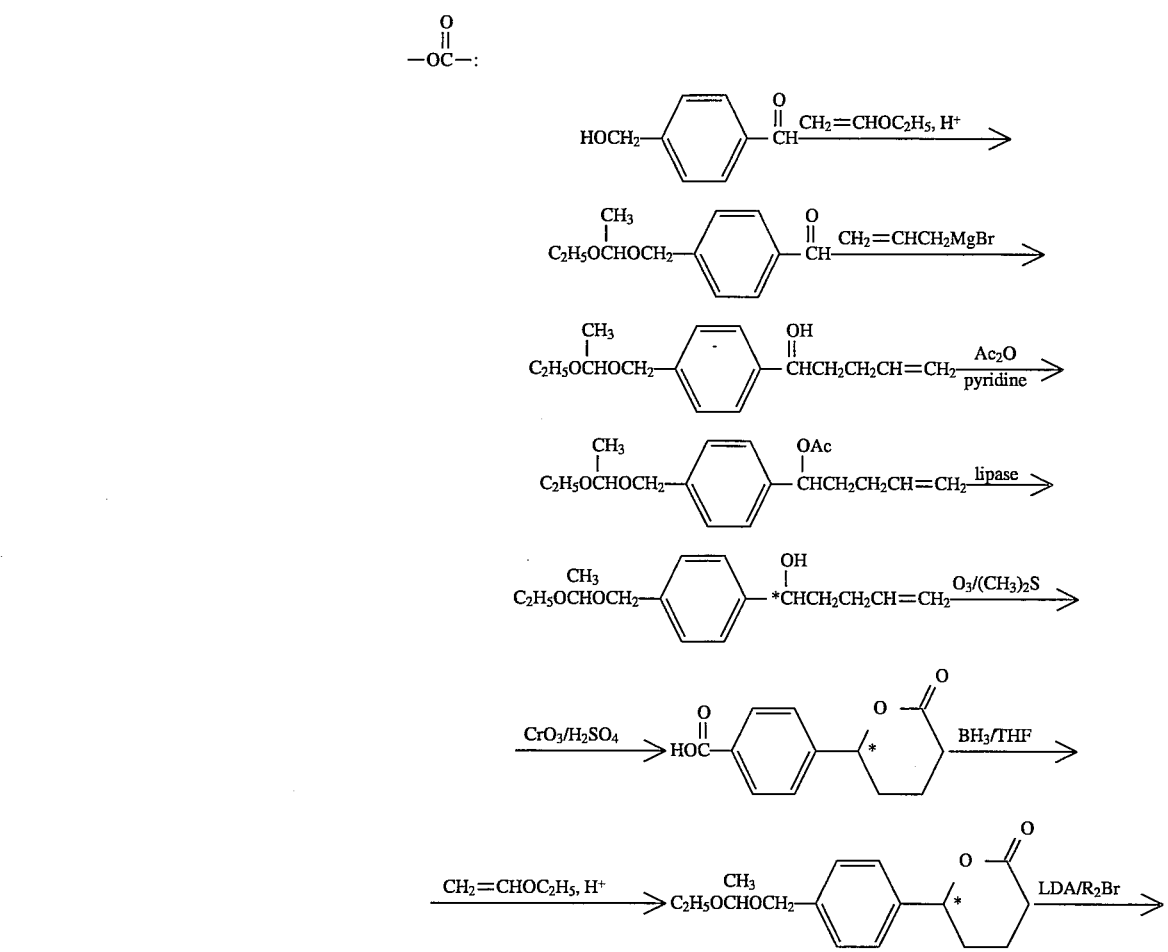

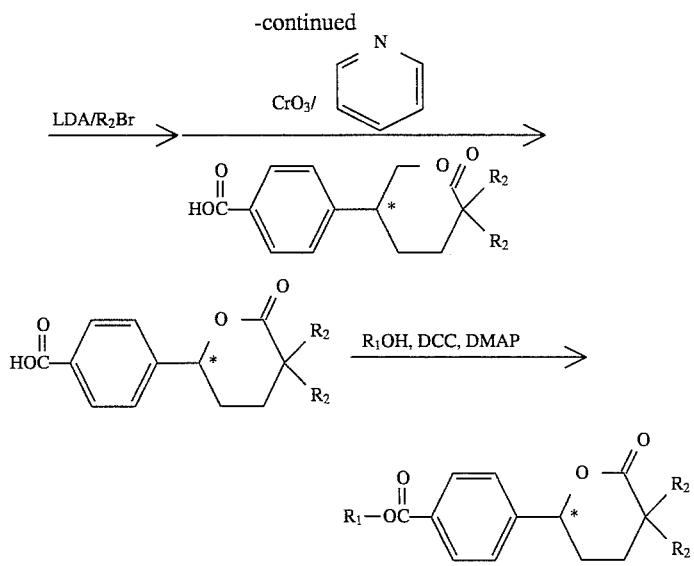

c) Where X is a direct bond:

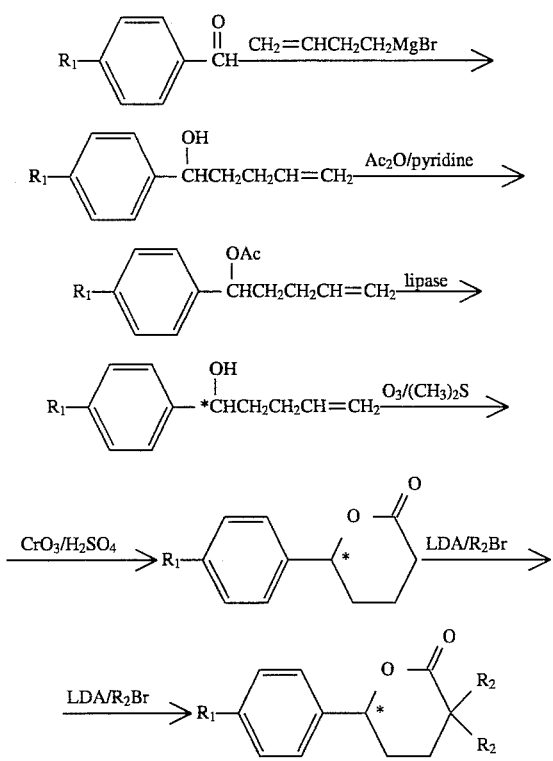

It is considered that a large dipole moment around the asymmetric carbon atom, the rotation of which is restricted, makes the greatest contribution to the manifestation of a spontaneous polarization or latent spontaneous polarization of a ferroelectric liquid crystal or a molecule as a material to be incorporated in a ferroelectric liquid crystal.

The optically active substances represented by the general formulae (1) and (2) have an asymmetric carbon fixed by a δ-valerolactone ring and can be regarded as a king of a mesogen.

In the case of the δ-valerolactone ring, it is known that the difference in the energy between the pseudo-boat conformation and the pseudo-chair conformation is as low as 0.54 kcal/mol in an unsubstituted form, so that the change of conformation easily occurs (see T. Philip, N. L. Allinger, J. Am. Chem. Soc., 103, 2151 (1981). By contrast, it is believed that the introduction of a substituent at the 2- and 5-positions makes it easy for the substances to take a pseudo-boat conformation in a cis form and a pseudo-chair conformation in trans form.

In this case, although a larger dipole moment is expected with respect to the pseudo-chair conformation because the lactone linkage is more close to the plane, no large spontaneous polarization can be expected with respect to the trans form because the trans form gives no asymmetry to the rotation around the major axis of the molecule.

When the form of 2,5,5-substituted δ-valerolactone and 2,2,5-substituted δ-valerolactone represented by the general formulae (1) and (2) is taken, however, it is believed that the δ-valerolactone ring becomes more easy to take a plane structure by virtue of the mutual action of the substituents at the 5,5-position and the mutual action of the substituents at the 2,2-position, so that the equilibrium is greatly shifted from the pseudo-boat conformation to the pseudo-chair conformation.

Further, when the 5,5-disubstituted form and 2,2-disubstituted form are taken, one substituent is present at the axial position where the steric hindrance to the rotation around the major axis of the molecule is larger. This results in a large spontaneous polarization. In other words, the present invention has an excellent feature that the use of the 5,5-disubstituted lactone and 2,2-disubstituted lactone enables a ferroelectric liquid crystal having a low melting point and a large spontaneous polarization to be obtained while fixing the conformation.

When the optically active compounds falling within the scope of the present invention are used alone, some of them show a liquid crystalline phase but the others do not. In even the compound not showing a liquid crystalline phase when used alone, the incorporation of such a compound into a non-chiral liquid crystal or liquid crystal composition showing the phase series of isotropic phase-nematic phase-smectic A phase-smectic C phase or isotropic phase-nematic phase-smectic C phase in such an amount as will not destroy the liquid crystallinity, that is, in an amount ranging from 0.1 to 90% by mole, enables a ferroelectric phase (a chiral smectic C phase) to be induced.

Accordingly, even a compound not showing the liquid crystal phase when used alone is valuable as an additive for a ferroelectric liquid crystal composition.

Where a liquid crystal is used in display devices, such as a display, the use of a plurality of liquid crystal compounds or a mixture of these liquid crystal compounds with additives is advantageous over the use of a single liquid crystal compound, because it is possible to vary the service temperature range (a temperature range in which a ferroelectric property is exhibited), the tilt angle, the helical pitch, the spontaneous polarization value, rotational viscosity, and other properties.

The liquid crystal composition of the present invention may comprise at least one optically active compound represented by the general formulae (1) and (2). Examples of the compound which may be mixed therewith include ferroelectric compounds and compositions and the above-described non-chiral liquid crystals or liquid crystal compositions. Preferred examples of compounds which can be mixed with the optically active compound represented by the general formulae (1) and (2) include the following compounds.

$$C_nH_{2n+1}O-X-\overset{O}{\underset{\|}{C}}O-Y-O*R \text{ wherein } n = 7\text{--}12,$$

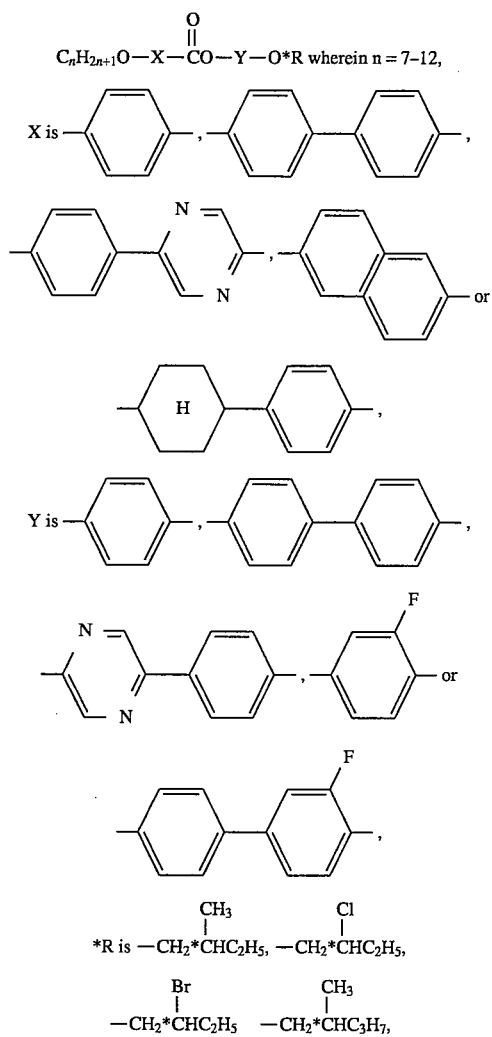

*R is $-CH_2*\underset{|}{\overset{CH_3}{C}}HC_2H_5$, $-CH_2*\underset{|}{\overset{Cl}{C}}HC_2H_5$, $-CH_2*\underset{|}{\overset{Br}{C}}HC_2H_5$, $-CH_2*\underset{|}{\overset{CH_3}{C}}HC_3H_7$, -continued $-CH_2*\underset{|}{\overset{F}{C}}HC_mH_{2m+1}$ (m = 5, 6, 8, 10 or 12), $-(CH_2)_2*\underset{|}{\overset{CF_3}{C}}HC_4H_9$, $-(CH_2)_3*\underset{|}{\overset{CH_3}{C}}HC_2H_5$, $-(CH_2)_3*\underset{|}{\overset{CH_3}{C}}HC_3H_7$, $-CH_2*\underset{|}{\overset{CH_3}{C}}HOC_{12}H_{25}$, $-(CH_2)_3*\underset{|}{\overset{CH_3}{C}}HOC_5H_{11}$, $-(CH_2)_5*\underset{|}{\overset{CH_3}{C}}HOC_5H_{11}$, $-*\underset{\|}{\overset{CH_3}{C}}HCOC_5H_{11}$ or $-CH_2*\underset{\|}{\overset{CH_3}{C}}HCOC_4H_9$.
$\phantom{XXXXXXXXXXXXX}O\phantom{XXXXXXXXXXX}O$ $$C_nH_{2n+1}O-X-\overset{O}{\underset{\|}{OC}}-Y-O*R$$

wherein n = 6, 8 or 10, X is 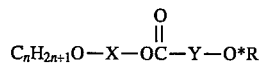,

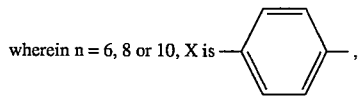 or

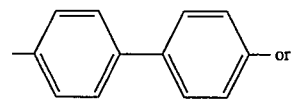, Y = 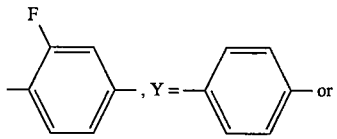 or

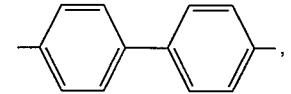,

*R is $-CH_2*\underset{|}{\overset{CH_3}{C}}HC_2H_5$, $-*\underset{|}{\overset{CH_3}{C}}HC_6H_{13}$, $-(CH_2)_3*\underset{|}{\overset{CH_3}{C}}HC_2H_5$, $-CH_2*\underset{|}{\overset{CH_3}{C}}HCH(CH_3)_2$, $-CH_2*\underset{|}{\overset{F}{C}}HC_8H_{17}$, $-CH_2*\underset{|}{\overset{CH_3}{C}}HOC_5H_{11}$, $-*\underset{\|}{\overset{CH_3}{C}}HCOC_8H_{17}$ or $-\underset{\|}{\overset{CH_3}{C}}*HOC_8H_{17}$.
$\phantom{XXXXX}O\phantom{XXXXXXX}O$ $$C_nH_{2n+1}-X-\overset{O}{\underset{\|}{C}}-O-Y-O*R \text{ wherein } n = 3, 7 \text{ or } 8,$$

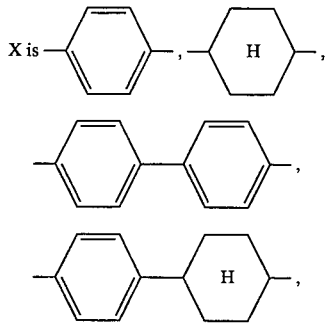

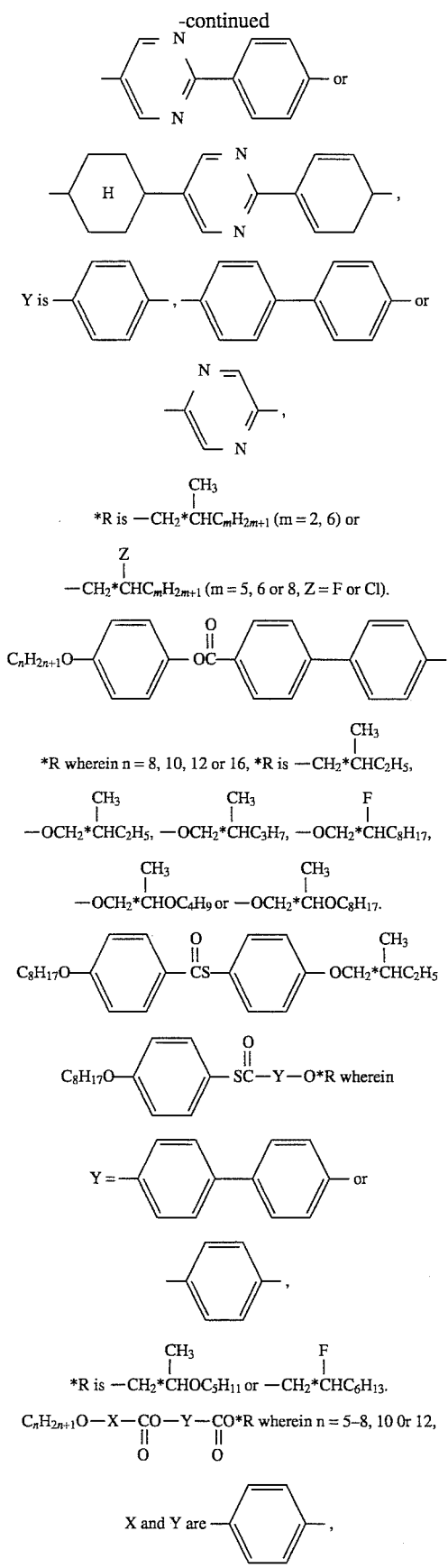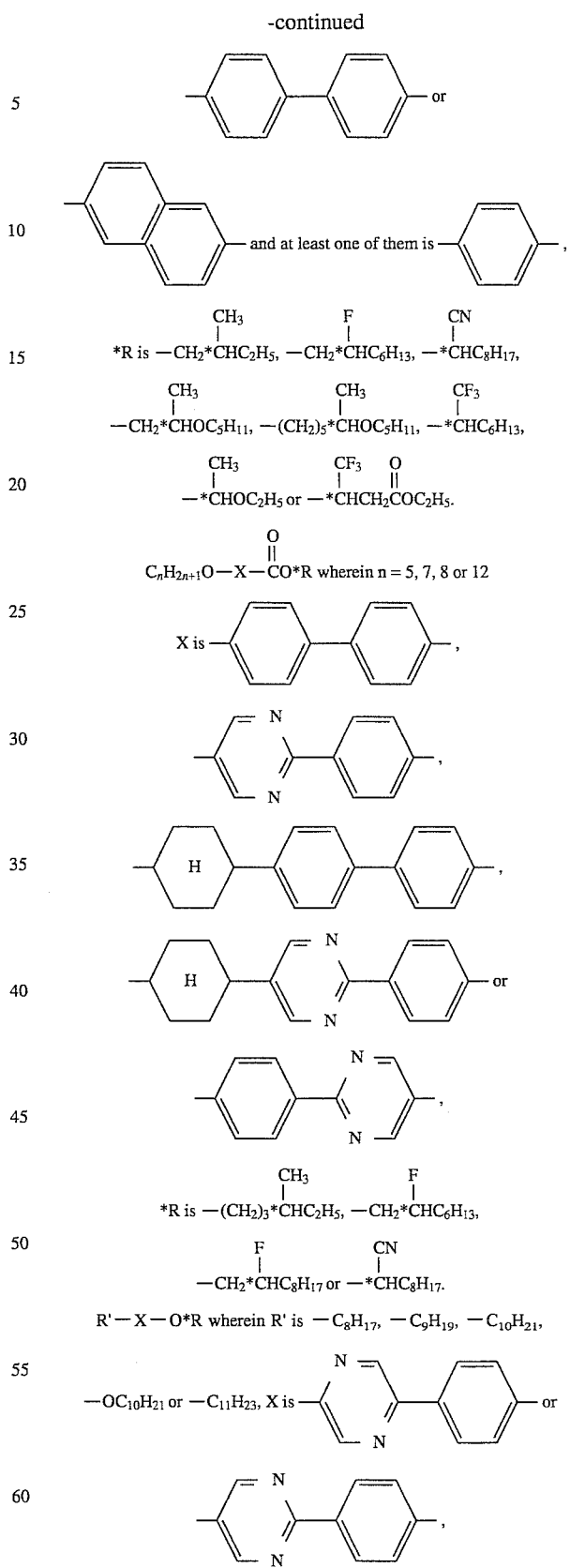

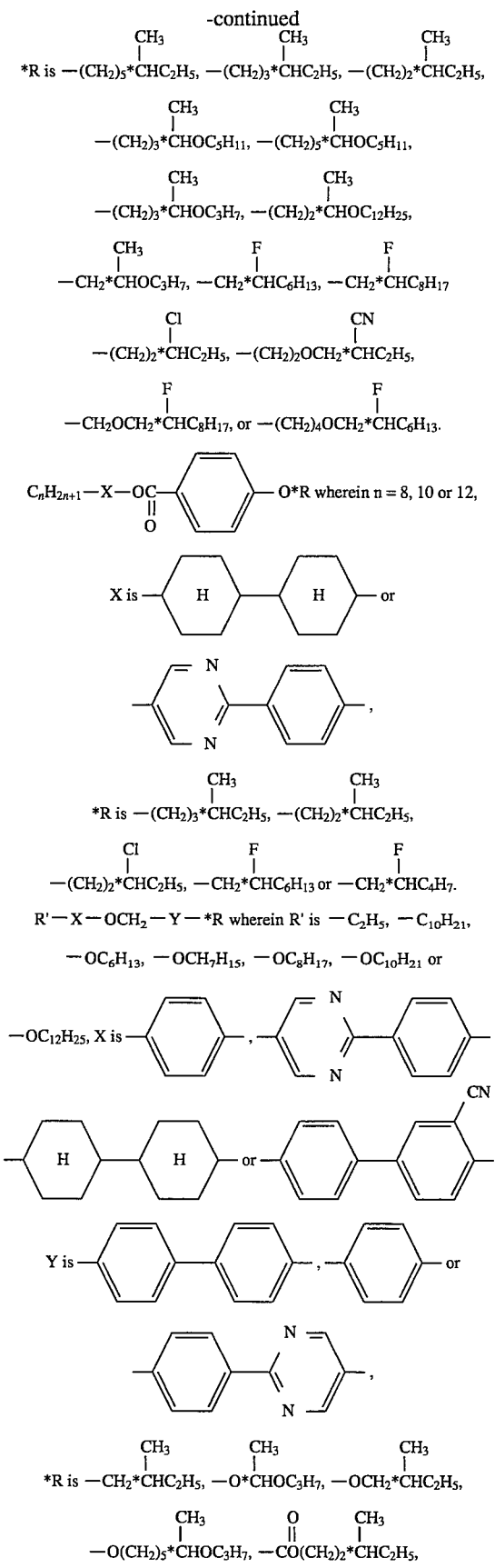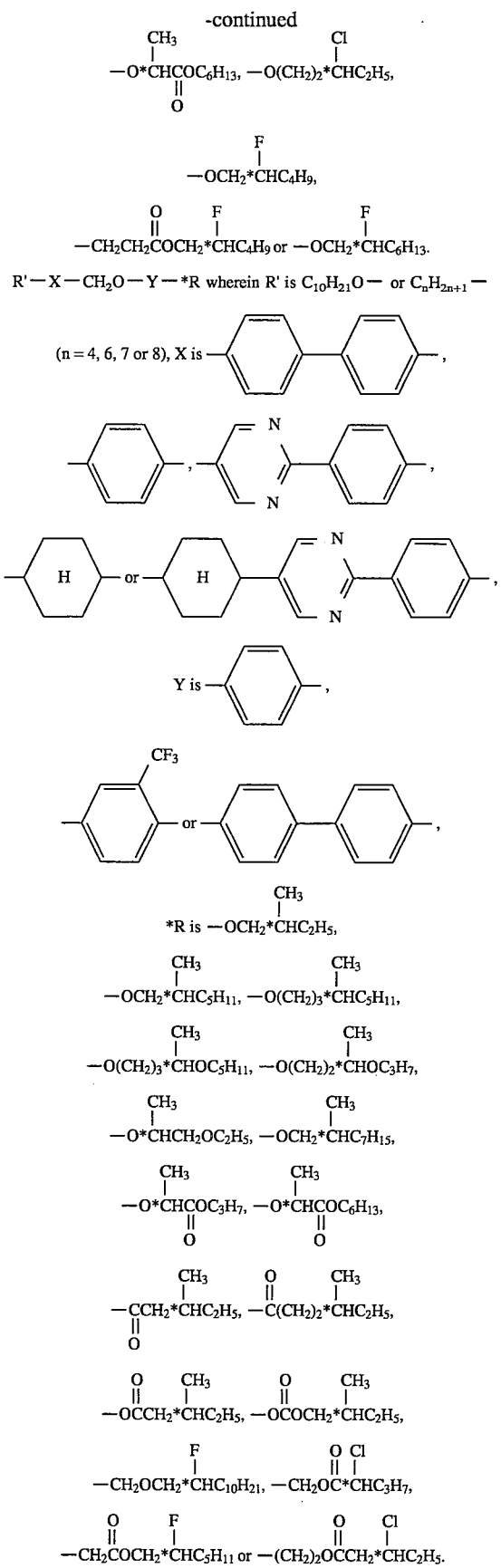

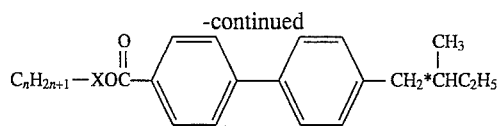

wherein n = 6 or 8, X is 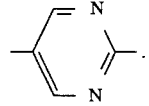 or

R'—X—OC*R wherein R' is —C$_{10}$H$_{21}$, —OC$_{10}$H$_{21}$ or

—OC$_8$H$_{17}$, X is 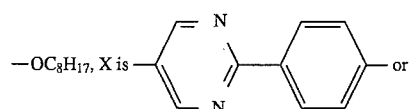 or

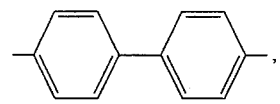,

*R is *CHC$_3$H$_7$ (Cl), —*CHC$_3$H$_7$ (Br), —*CHC$_8$H$_{17}$ (F),
—CH$_2$*CHC$_4$H$_9$ (CF$_3$), —*CHOC$_8$H$_{17}$ (CH$_3$) or —(CH$_2$)$_2$*CHOC$_5$H$_{11}$ (CH$_3$).

C$_n$H$_{2n+1}$OC(=O)—X—OC(=O)—Y—O*R wherein n = 6 or 10,

X is 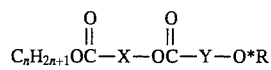,

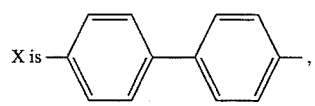,

Y is 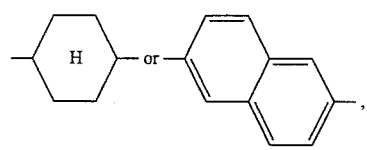,

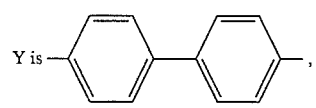,

*R is CH$_2$*CHOC$_5$H$_{11}$ (CH$_3$), —CH$_2$*CHOC$_8$H$_{17}$ (CH$_3$), —CH$_2$*CHC$_6$H$_{13}$ (F) or
—CH$_2$*CHCH(CH$_3$)$_2$ (Cl).

C$_n$H$_{2n+1}$—X—CO—Y—CO*R wherein n = 5 or 8,

X is 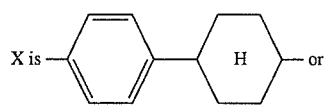 or

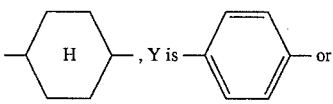, Y is 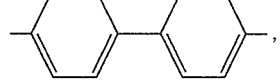 or

,

*R is —(CH$_2$)$_2$*CHOC$_5$H$_{11}$ (CH$_3$) or —*CHC(=O)OC$_5$H$_{11}$ (CH$_3$).

C$_{10}$H$_{21}$O—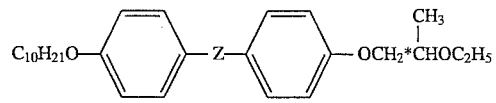—OCH$_2$*CHOC$_2$H$_5$ (CH$_3$)

wherein Z is —(CH$_2$)$_2$—, —CH$_2$C(=S)— or —(CH$_2$)$_2$C(=O)—.

C$_n$H$_{2n+1}$—X—CO—Y—*R wherein n = 8, 10 or 12,

X is 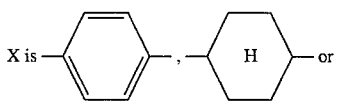 or

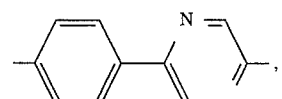,

Y is 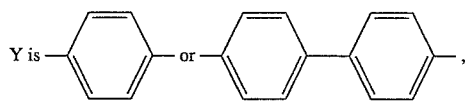,

*R is —CH$_2$*CHC$_2$H$_5$ (CH$_3$), —CH$_2$*CHC$_6$H$_{13}$ (F) or
—OCO*CHC$_2$H$_5$ (Cl).

C$_n$H$_{2n+1}$—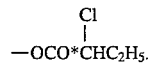—O*R wherein n = 8 or 10,

*R is —CH$_2$*CHC$_8$H$_{17}$ (F) or —CH$_2$*CHC$_3$H$_7$ (CH$_3$).

R—CO—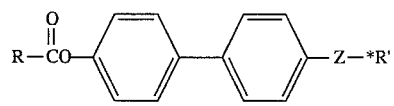—Z—*R' wherein R is —C$_8$H$_{17}$ or

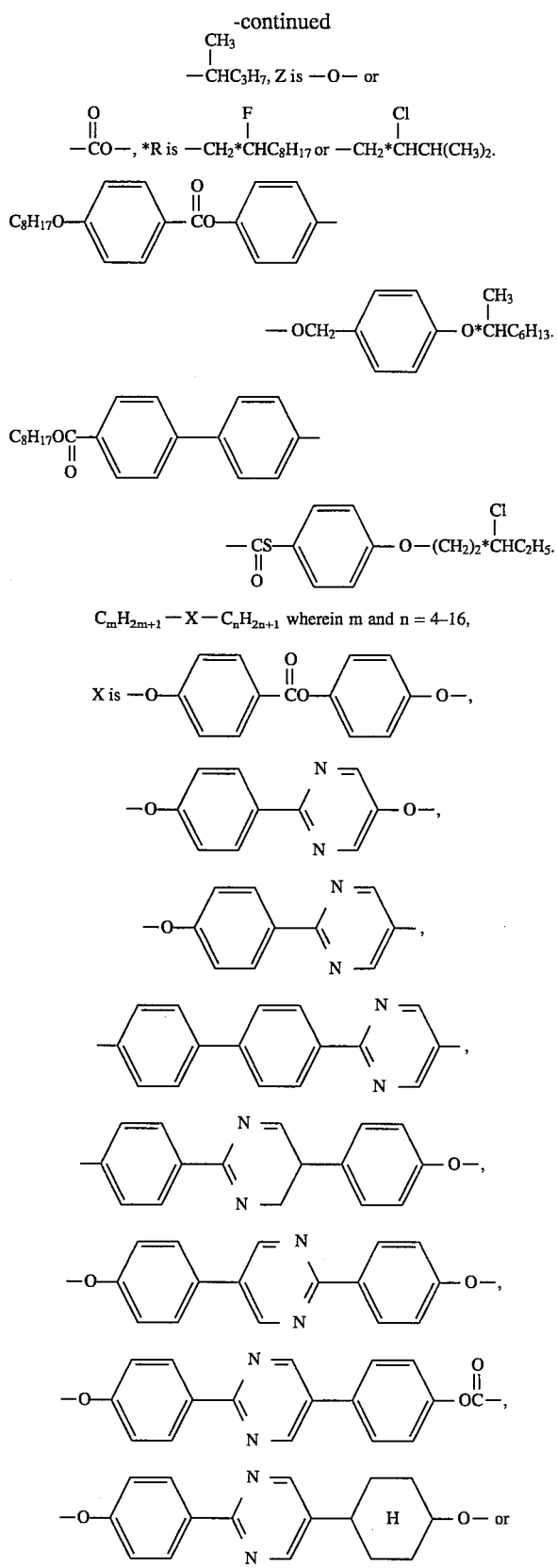

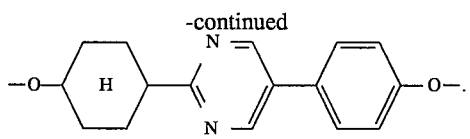

In the optically active compound of the present invention, one having a liquid crystallinity exhibits a high spontaneous polarization as a ferroelectric liquid crystal and excellent performance, i.e., no coloring, excellent chemical stability, such as hydrolysis resistance, and good light stability, and even one having no liquid crystallinity, when used as an additive for mixing into a non-ferroelectric liquid crystal composition to prepare a ferroelectric liquid crystal composition or as a component to be incorporated into a ferroelectric liquid crystal composition, has excellent properties, i.e., is useful for enhancing the spontaneous polarization of the composition and improving the response speed, and in the addition and incorporation thereof brings about no coloring of the composition and no lowering in the chemical or light stability. The liquid crystal composition of the present invention also has the above-described performance.

EXAMPLES

The present invention will now be described in more detail by way of the following Examples. The present invention, however, is not limited to these Examples only.

REFERENTIAL EXAMPLE 1

Synthesis of t-butyl (S)-γ-butyrolactone-γ-carboxylate (S)-γ-butyrolactone-γ-carboxylic acid was synthesized according to the process of D. L. Coffen et al (J. Org. Chem., 1988, 53, pages 4780–4786). Namely, 147 g of L-glutamic acid was suspended in 500 ml of water, and a solution of 104 g of sodium nitrite dissolved in 144 ml of water and 250 ml of 5.6N hydrochloric acid were simultaneously dropwise added to the suspension with vigorous stirring over a period of more than 5 hr.

During the dropwise addition, the reaction temperature was maintained at 15° to 20° C.

After the completion of the dropwise addition, the reaction mixture was stirred at room temperature overnight, and water was then distilled off under a reduced pressure while maintaining the temperature not above 40° C. Ethyl acetate was added to the residue, and the mixture was dried over magnesium sulfate.

The dried mixture was filtered, and 20 g of an acid type ion exchange resin (Amberlite IR-120B) was added to the filtrate to remove the remaining glutamic acid. Then, the mixture was filtered, and the solvent was distilled off from the filtrate under a reduced pressure. The remaining water was removed by azeotropic distillation with benzene.

Methylene chloride was added to the residue, and crystallization was effected in a refrigerator to obtain 74 g of (S)-γ-butyrolactone-γ-carboxylic acid. The compound thus obtained was suspended in 200 ml of ether, 25 g of an acid type ion exchange resin (Amberlite IR-120B) was added to the suspension, the mixture was cooled to −20° C., 60 ml (1.2 equivalents) of isobutylene was added to the mixture, and the mixture was stirred at 0° C. for 4 hr for a reaction. After the reaction, solid matter was removed by filtration, and isobutylene and ether was distilled off from the filtrate. The residue was subjected to vacuum distillation to obtain t-butyl (S)-γ-butyrolactone-γ-carboxylate [120° to 123° C./4 mmHg, $[\alpha]_D$ (23.5° C.)=+4.81 (C=0.935, CHCl$_3$)].

REFERENTIAL EXAMPLE 2

Synthesis of (S)-2,2-dimethyl-5-hydroxymethyl-valerolactone

In 150 ml of 3,3-dimethoxypentane was dissolved 25 g of (S)(−)-butanetriol, and 0.1 g of p-toluenesulfonic acid was added to the solution. The solution was stirred for 16 hr to conduct a reaction. The resultant reaction mixture was poured into a saturated aqueous solution of sodium hydrogencarbonate, the reaction product was extracted with an ether, and the extract was washed with a saturated saline solution. The solvent was distilled off from the extract as washed, and the resultant residue was purified by a silica gel column chromatography through the use of hexane-ethyl acetate as a developing solvent to obtain 26.5 g of (S)-2,2-diethyl-4-(2-hydroxyethyl)-1,3-dioxolane. The whole quantity of the product was dissolved in 500 ml of benzene, and 24 g of imidazole, 100 g of triphenylphosphine and 40 g of iodine were added to the solution. The mixture was stirred for 2 hr and then poured into ice water. The reaction product was extracted with an ether, and the extract was well washed with a 10% aqueous solution of sodium thiosulfate and dried over magnesium sulfate. The solvent was removed from the dried reaction product by distillation, and the resultant residue was purified by a silica gel column chromatography through the use of hexane-ethyl acetate as a developing solvent to obtain 31 g of (S)-2,2-diethyl-4-(2-iodoethyl)-1,3-dioxolane.

Then, 80 ml of a solution (1.55 mol/liter) of n-butyl-lithium in hexane was dropwise added to a mixed solution comprising 9.2 g of diisopropylamine and 100 ml of anhydrous THF at 0° C. in an argon gas stream, and 5 g of isobutyric acid was then dropwise added thereto. After the completion of the dropwise addition, the mixture was stirred at 0° C. for additional 10 min, 10 ml of hexamethylphosphoramide was added thereto, the mixture was stirred at 10° C. for 30 min, 16 g of (S)-2,2-diethyl-4-(2-iodoethyl)-1,3-dioxolane was added thereto at 0° C., and the mixture was stirred for 2 hr while maintaining the temperature at 0° C. To the reaction mixture was added 10 ml of water, and the pH value was adjusted to 5 with 1N hydrochloric acid. The reaction product was extracted with an ether, the extract was washed with a saturated saline solution and dehydrated over magnesium sulfate, the solvent was removed by distillation, and the resultant residue was purified by a silica gel column chromatography through the use of hexane-ethyl acetate as a developing solvent. The purified product was dissolved in THF, a few drops of 6N hydrochloric acid was added to the solution, and the mixture was stirred for 15 min, thereby eliminating a protecting group. The product was then poured into water and extracted with ethyl acetate, the extract was washed with a saturated saline solution, the solvent was removed from the extract by distillation, the resultant residue was dissolved in benzene, a small amount of p-toluenesulfonic acid was added thereto, water was removed from the mixture by azeotropic distillation, the mixture was poured into a saturated aqueous solution of sodium hydrogencarbonate, and the reaction product was extracted with an ether. The extract was washed with a saturated saline solution and dried over magnesium sulfate, the solvent was removed from the dried extract by distillation, and the residue was purified by a silica gel column chromatography through the use of hexane-ethyl acetate as a developing solvent to obtain 3.5 g of (S)-2,2-dimethyl-5-hydroxymethyl-valerolactone.

REFERENTIAL EXAMPLE 3

Synthesis of (S)-5-hydroxymethyl-valerolactone

To a solution of 0.55 g of sodium in 20 ml of absolute ethanol were added 6 g of (S)-2,2-diethyl-4-(2-iodoethyl)-1,3-dioxolane synthesized in Example 1 and 3.7 g of diethyl malonate, and the mixture was refluxed for 2 hr. Then, 50 ml of an ether and 50 ml of water were successively added to the resultant solution, and the ether phase was collected. The resultant ether solution was washed with a saturated saline solution, dried over magnesium sulfate, the solvent was removed from the dried ether solution by distillation, and the resultant residue was purified by a silica gel column chromatography through the use of hexane-ethyl acetate as a developing solvent. The purified product was dissolved in an ether, and 2N sodium hydroxide was added thereto. The mixture was refluxed for hydrolysis and decarboxylation, the pH was adjusted to 5 with 1N hydrochloric acid, and the reaction product was extracted with ethyl acetate. The solvent was removed from the extract, the resultant residue was dissolved in THF, a few drops of sulfuric acid was added thereto, the solution was concentrated, and the solute was purified from the concentrate by a silica gel column chromatography through the use of a mixed solution comprising hexane and ethyl acetate as a developing solution to obtain 0.7 g of (S)-5-hydroxymethyl-valerolactone.

EXAMPLE 1

Synthesis of (R)-2-(4'-octyloxybiphenyl-4-carboxy)-5,5-dimethyl-δ-valerolactone

In absolute methanol were dissolved 5.2 g of β-hydroxyisovaleric acid and 15.2 g of monoethyl acetylmalate, and 0.14 g of sodium hydroxide was added to the solution. The mixture was subjected to Kolbe electrolysis by applying a voltage of ±20 V for 5 hr through the use of a platinum electrode. After the reaction, 8 g of sodium hydroxide was added to the reaction mixture, and 200 ml of a mixed solution comprising water and methanol (1:1) was added thereto. The mixture was allowed to stand overnight for hydrolysis. A major portion of methanol contained in the solution was removed by distillation, and a neutral component contained in the solution was extracted with diethyl ether, and hydrochloric acid was added to the remaining aqueous alkaline solution to adjust the pH to 1. Thereafter, sodium chloride was added thereto until a saturated solution was prepared, and the reaction product was extracted with chloroform. The resultant chloroform solution was washed with water and dried over magnesium sulfate, and the chloroform was removed by distillation under a reduced pressure. Then 8.3 g of the crude product thus obtained was dissolved in 150 ml of benzene, 0.1 g of p-toluenesulfonic acid was added thereto, and the mixture was refluxed for 5 hr. The refluxed solution was cooled to room temperature and extracted with an ether, and the extract was washed with a saturated aqueous solution of sodium hydrogencarbonate and then with water, and the solvent was removed from the extract by distillation under a reduced pressure to obtain a crude product. The crude product was purified by a silica gel column chromatography to obtain 5.2 g of (S)-2-hydroxy-5,5-dimethyl-δ-valerolactone.

Then, 0.2 g of the (S)-2-hydroxy-5,5-dimethyl-δ-valerolactone was suspended in 5 ml of dried benzene together with 0.25 g of 4'-octyloxybiphenyl-4-carboxylic acid, 0.05 ml of diethyl azodicarboxylate and 0.3 g of triphenylphosphine were successively added to the suspension, and a reaction was allowed to proceed at room temperature overnight. The reaction mixture was concentrated, and the concentrate was purified by a silica gel column chromatography to obtain 0.3 g of (R)-2-(4'-octyloxybiphenyl-4-carboxy)-5,5-dimethyl-δ-valerolactone.

$^1$HNMR=8.12 (2Hd), 7.60 (4Hq), 6.98 (2Hd), 5.47 (1Hd, d), 4.02 (2H, t), 1.1–2.5 (18H, m), 0.90 (3H, t)

Derivatives represented by the general formula (1) wherein both the two $R_2$'s represent either a hydrogen atom or an alkyl group having 2 to 18 carbon atoms can be synthesized in the same manner as that described above, except that instead of the β-hydroxyisovaleric acid, use is made of 3-hydroxypropionic acid, 3-ethyl-3-hydroxypentanoic acid, 3-propyl-3-hydroxyhexanoic acid or a straight-chain aliphatic carboxylic acid having 7 to 15 carbon atoms wherein the two hydrogens at the 3-position are substituted with an alkyl group having 4 to 12 carbon atoms and a hydroxyl group, respectively.

Further, derivatives represented by the general formula (1) wherein $R_1$ represents a straight-chain or branched alkyl group having 1 to 18 carbon atoms or alkenyl group having 2 to 18 carbon atom, an alkoxyalkyl group having 1 to 18 carbon atoms and comprising an alkoxy group having 1 to 3 carbon atoms, or the above-described groups substituted with a halogen, X represents an ether linkage, a direct bond, a carbonyloxy group or an oxycarbonyl group, A represents a biphenyl and Y represents a carbonyloxy group can be synthesized in the same manner as that described above, except that instead of the 4'-octyloxybiphenyl-4-carboxylic acid, use is made of a straight chain alkoxybiphenyl-4-carboxylic acid comprising an alkoxy group having 1 to 7 or 9 to 18 carbon atoms, a branched alkoxybiphenyl-4-carboxylic acid comprising an alkoxy group having 3 to 18 carbon atoms, an alkoxyalkyloxybiphenyl-4-carboxylic acid comprising alkyloxy group having 1 to 18 carbon atoms and an alkoxy group having 1 to 3 carbon atoms, a straight-chain or branched alkenyloxybiphenyl-4-carboxylic acid comprising an alkenyl group having 2 to 18 carbon atoms, a straight-chain or branched alkylbiphenyl-4-carboxylic acid comprising an alkyl group having 1 to 18 carbon atoms, a straight-chain or branched alkenylbiphenyl-4-carboxylic acid comprising an alkenyl group having 2 to 18 carbon atoms, an alkoxyalkylbiphenyl-4-carboxylic acid comprising an alkyl group having 1 to 18 carbon atoms and an alkoxy group having 1 to 3 carbon atoms, a straight-chain or branched alkoxycarbonylbiphenyl-4-carboxylic acid comprising an alkoxy group having 1 to 18 carbon atoms, a straight-chain or branched alkenyloxycarbonylbiphenyl-4-carboxylic acid comprising an alkenyl group having 2 to 18 carbon atoms, an alkoxyalkyloxycarbonylbiphenyl-4-carboxylic acid comprising alkyl group having 1 to 18 carbon atoms and an alkoxy group having 1 to 3 carbon atoms, a straight-chain or branched alkylcarbonyloxybiphenyl-4-carboxylic acid comprising an alkyl group having 1 to group 18 carbon atoms, a straight-chain or branched alkenylcarbonyloxybiphenyl-4-carboxylic acid comprising an alkenyl group having 2 to 18 carbon atoms, an alkoxyalkylcarbonyloxybiphenyl-4-carboxylic acid comprising alkyl group having 1 to 18 carbon atoms and an alkoxy group having 1 to 3 carbon atoms, a halogen-substituted alkoxybiphenyl-4-carboxylic acid, a halogen-substituted alkylbiphenyl-4-carboxylic acid, a halogen-substituted alkoxycarbonylbiphenyl-4-carboxylic acid, a halogen-substituted alkylcarbonyloxybiphenyl-4-carboxylic acid, a halogen-substituted alkenyloxybiphenyl-4-carboxylic acid or a halogen-substituted alkoxyalkyloxybiphenyl-4-carboxylic acid.

Further, derivatives represented by the general formula (1) wherein A represents phenyloxymethylphenyl can be synthesized in the same manner as that described above, except that instead of the 4'-octyloxybiphenyl-4-carboxylic acid, use is made of a straight-chain or branched alkoxyphenyloxymethylphenyl-4-carboxylic acid comprising an alkoxy group having 1 to 18 carbon atoms, an alkoxyalkyloxyphenyloxymethylphenyl-4-carboxylic acid comprising an alkyl group having 1 to 18 carbon atoms and an alkoxy group having 1 to 3 carbon atoms, a straight-chain or branched alkenyloxyphenyloxymethylphenyl-4-carboxylic acid alkenyl group thereof having 2 to 18 carbon atoms, a straight-chain or branched alkylphenyloxymethylphenyl-4-carboxylic acid alkyl group thereof having 1 to 18 carbon atoms, an alkoxyalkylphenyloxymethylphenyl-4-carboxylic acid comprising an alkyl group having 1 to 18 carbon atoms and an alkoxy group having 1 to 3 carbon atoms, a straight-chain or branched alkenylphenyloxymethylphenyl-4-carboxylic acid comprising an alkenyl group having 2 to 18 carbon atoms, a straight-chain or branched a alkoxycarbonylphenyloxymethylphenyl-4-carboxylic acid comprising an alkoxy group having 1 to 18 carbon atoms, an alkoxyalkyloxycarbonylphenyloxymethylphenyl-4-carboxylic acid comprising an alkyl group having 1 to 18 carbon atoms and an alkoxy group having 1 to 3 carbon atoms, a straight-chain or branched alkenyloxycarbonylphenyloxy- methylphenyl-4-carboxylic acid comprising an alkenyl group having 2 to 18 carbon atoms, a straight-chain or branched alkylcarbonyloxyphenyloxymethylphenyl-4-carboxylic acid comprising an alkyl group having 1 to 18 carbon atoms, an alkoxyalkylcarbonyloxyphenyloxymethylphenyl-4-carboxylic acid comprising alkyl group having 1 to 18 carbon atoms and an alkoxy group having 1 to 3 carbon atoms, a straight-chain or branched alkenylcarbonyloxyphenyloxymethylphenyl-4-carboxylic acid comprising an alkenyl group having 2 to 18 carbon atoms, a halogen-substituted alkoxyphenyloxymethylphenyl-4-carboxylic acid, a halogen-substituted alkoxycarbonylphenyloxymethylphenyl-4-carboxylic acid, a halogen-substituted alkenyloxyphenyloxymethylphenyl-4-carboxylic acid or a halogen-substituted alkoxyalkyloxyphenyloxymethylphenyl-4-carboxylic acid.

Further, derivatives represented by the general formula (1) wherein A represents benzyloxyphenyl, phenylcarbonyloxyphenyl or phenyloxycarbonylphenyl can be synthesized through the use of a benzyloxyphenyl-4-carboxylic acid derivative, a phenylcarbonyloxyphenyl-4-carboxylic acid derivative or a phenyloxycarbonylphenyl-4-carboxylic acid derivative instead of the above-described phenyloxymethylphenyl-4-carboxylic acid derivative which is an alternative to the 4'-octyloxybiphenyl-4-carboxylic acid.

Similarly, derivatives represented by the general formula (1) wherein Y represents an ether linkage can be synthesized through the use of an alcohol derivative instead of the carboxylic acid derivative.

EXAMPLE 2

Synthesis of
(2R)-2-(4'-octyloxybiphenyloxymethyl)-5,5-dimethyl-δ-valerolactone and (2S)-2-(4'-octyloxybiphenyloxymethyl)-5,5-dimethyl-δ-valerolactone In 50 ml of 7 wt. % hydrochloric acid methanol solution was dissolved 1.18 g of β-hydroxyisovaleric acid, and an reaction was allowed to proceed at room temperature overnight. The solvent was removed from the solution as reacted by distillation under a reduced pressure to obtain 1.30 g of crude methyl β-hydroxyisovalerate. The crude methyl β-hydroxyisovalerate was dissolved in diethyl ether, and 0.91 g of 3,4-dihydro-2H-pyran and a catalytic amount of p-toluenesulfonic acid were added thereto. Stirring was continued at room temperature overnight for reaction. The resultant reaction mixture was washed with a saturated aqueous solution of sodium hydrogencarbonate and then with water and dried over magnesium sulfate. The solvent was removed from the dried reaction mixture by distillation under a reduced pressure to obtain 1.98 g of crude methyl β-dihydropyranyloxyisovalerate.

Thereafter, 0.7 g of lithium aluminum hydride was suspended in 20 ml of diethyl ether, and a solution of 1.98 g of methyl β-dihydropyranyloxyisovalerate in 3 ml of diethyl ether was slowly dropwise added to the suspension, and a reaction was allowed to proceed at room temperature overnight. The mixture was further heated and refluxed for 1 hr and then cooled, and 0.7 ml of water, 0.7 ml of a 15% aqueous sodium hydroxide solution and 2.1 ml of water were successively added in that order with ice cooling. The mixture was stirred at room temperature for 1 hr, 20 ml of tetrahydrofuran was added thereto, and the mixture was stirred for additional one hr. The precipitat was collected by filtration and washed with 10 ml of tetrahydrofuran, and the washing was combined with the filtrate. The solvent was removed from the combined filtrate and washing by distillation under a reduced pressure to obtain 1.32 g of crude 3-dihydropyranyloxy-3-methyl butanol.

The crude product was dissolved in 5 ml of dichloromethane, and 3.76 g of carbon tetrabromide was added to the solution. A solution of 1.95 g of triphenylphosphine in 10 ml of dichloromethane was slowly dropwise added thereto while stirring, and a reaction was allowed to proceed at room temperature for 2 hr while stirring the mixture. The reaction mixture was poured into 200 ml of pentane, and a pentane phase was recovered by decantation. The recovered pentane solution was washed with a saturated aqueous solution of sodium hydrogencarbonate and then with water and dried over magnesium sulfate, and the solvent was removed from the dried solution by distillation under a reduced pressure. The residue was purified by vacuum distillation to obtain 1.71 g of purified 3-dihydropyranyloxy-3-methylbutyl bromide.

Then, 0.17 g of sodium was dissolved in 10 ml of dried ethanol, 1.17 g of ethyl malonate was added thereto, 1.71 g of 3-dihydropyranyloxy-3-methylbutyl bromide was slowly dropwise added thereto, and the mixture was stirred at room temperature for 2 hr and then refluxed for 2 hr to conduct a reaction. The reaction mixture was cooled to room temperature, and the solid matter was removed by filtration. The filtrate was evaporated to dryness. The solid thus obtained was dissolved in 30 ml of benzene, a catalytic amount of p-toluenesulfonic acid was added thereto, and the mixture was refluxed for 3 hr. After the completion of the reaction, the reaction mixture was cooled to room temperature, washed with a saturated aqueous solution of sodium hydrogencarbonate and then with water and dried over magnesium sulfate, and the solvent was removed from the dried solution by distillation under a reduced pressure to obtain a crude product. The crude product was purified by a silica gel column chromatography to obtain 0.47 g of ethyl 5,5-dimethyl-δ-valerolactone-2-carboxylate.

Thereafter, 0.06 g of sodium borohydride was suspended in 2 ml of ethanol, a solution of 0.47 g of ethyl 5,5-dimethyl-δ-valerolactone-2-carboxylate in 2 ml of ethanol was slowly dropwise added thereto, the mixture was stirred at room temperature for 10 min, the pH value was adjusted to 3 with 10% hydrochloric acid, insolubles were removed by filtration, and the filtrate was evaporated to dryness to obtain 0.45 g of crude 2-hydroxymethyl-5,5-dimethyl-δ-valerolactone.

The crude product was dissolved in 2 ml of pyridine, 0.81 g of p-toluenesulfonyl chloride was added thereto, the mixture was stirred at room temperature overnight for a reaction. After the completion of the reaction, the reaction mixture was poured into dilute hydrochloric acid with ice cooling, the reaction product was extracted with diethyl ether, the extract was washed with dilute hydrochloric acid and then with water and dried over magnesium sulfate, the solvent was removed by distillation under a reduced pressure to obtain a crude product, and the crude product was purified by a silica gel column chromatography to obtain 0.70 g of 2-tosyloxymethyl-5,5-dimethyl-δ-valerolactone.

The product was dissolved in 10 ml of acetone, 0.48 g of sodium iodide was added thereto, and the mixture was refluxed for 10 hr to conduct a reaction. The reaction mixture was evaporated to dryness by distillation under a reduced pressure, and the reaction product was extracted with diethyl ether. The extract was washed three times with water and dried over magnesium sulfate, and the solvent was removed by distillation under a reduced pressure to obtain 0.60 g of crude 2-iodomethyl-5,5-dimethyl-δ-valerolactone.

Thereafter, 0.09 g of 60% sodium hydride was suspended in 5 ml of dimethylformamide, and a solution of 0.63 g of 4'-octyloxybiphenol in 5 ml of dimethylformamide was added to the suspension, and the mixture was stirred at room temperature for 1 hr to conduct a reaction. To the resultant solution was added 0.60 g of 2-iodomethyl-5,5-dimethyl-δ-valerolactone, and stirring was continued at room temperature for two days to conduct a reaction. The reaction mixture was poured into ice water, and the reaction product was extracted with diethyl ether. The extract was washed three times with water and dried over magnesium sulfate, the solvent was removed by distillation under a reduced pressure to obtain a crude product, and the crude product was purified by a silica gel column chromatography to 0.58 g of 2-(4'-octyloxybiphenyloxymethyl)-5,5-dimethyl-δ-valerolactone. The product was subjected to optical resolution by a liquid chromatography, and both components thus obtained were each recrystallized from ethanol to obtain 0.20 g of (2R)-2-(4'-octyloxybiphenyloxymethyl)-5,5-dimethyl-δ-valerolactone and 0.11 g of (2S)-2-(4'-octyloxybiphenyloxymethyl)-5,5-dimethyl-δ-valerolactone, respectively.

Both the compounds exhibited the following phase transition behavior.

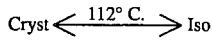

Derivatives represented by the general formula (1) wherein two $R_2$'s are hydrogen atoms, or alkyl groups having 2 to 18 carbon atoms can be synthesized in the same manner as that described above, except that instead of the β-hydroxyisovaleric acid, use is made of 3-hydroxypropionic acid, 3-ethyl-3-hydroxypentanoic acid, 3-propyl-3-hydroxyhexanoic acid or a straight-chain aliphatic carboxylic acid having 7 to 15 carbon atoms wherein the two hydrogens at the 3-position are substituted with an alkyl group having 4 to 12 carbon atoms and a hydroxyl group, respectively.

Further, derivatives represented by the general formula (1) wherein $R_1$ represents a straight-chain or branched alkyl group having 1 to 18 carbon atoms or alkenyl group, having 2 to 18 carbon atoms, an alkoxyalkyl group comprising an alkyl group having 1 to 18 carbon atoms and an alkoxy group having 1 to 3 carbon atoms or the above-described groups substituted with a halogen, X represents an ether linkage, a direct bond, a carbonyloxy group or an oxycarbonyl group, A represents a biphenyl and Y represents a carbonyloxy group can be synthesized in the same manner as that described above, except that instead of the 4'-octyloxybiphenol, use is made of a straight chain alkoxybiphenol comprising an alkoxy group having 1 to 7 or 9 to 18 carbon atoms, a branched alkoxybiphenol comprising an alkoxy group having 3 to 18 carbon atoms, an alkoxyalkyloxybiphenol comprising an alkyl group having 1 to 18 carbon atoms and an alkoxy group having 1 to 3 carbon atoms, a straight-chain or branched alkenyloxybiphenol comprising an alkenyl group having 2 to 18 carbon atoms, a straight-chain or branched alkylbiphenol comprising an alkyl group having 1 to 18 carbon atoms, a straight-chain or branched alkenylbiphenol comprising alkneyl group having 2 to 18 carbon atoms, an alkoxyalkylbiphenol comprising an alkyl group having 1 to 18 carbon atoms and an alkoxy group having 1 to 3 carbon atoms, a straight-chain or branched alkoxycarbonylbiphenol comprising an alkoxy group having 1 to 18 carbon atoms, a straight-chain or branched alkenyloxycarbonylbiphenol comprising an alkenyl group having 2 to 18 carbon atoms, an alkoxyalkyloxycarbonylbiphenol comprising an alkyl group having 1 to 18 carbon atoms and an alkoxy group having 1 to 3 carbon atoms, a straight-chain or branched alkylcarbonyloxybiphenol comprising an alkyl group having 1 to 18 carbon atoms, a straight-chain or branched alkenylcarbonyloxybiphenol comprising an alkenyl group having 2 to 18 carbon atoms, an alkoxyalkylcarbonyloxybiphenol comprising an alkyl group having 1 to 18 carbon atoms and an alkoxy group having 1 to 3 carbon atoms, a halogen-substituted alkoxybiphenol, a halogen-substituted alkylbiphenol, a halogen-substituted alkoxycarbonylbiphenol, a halogen-substituted alkylcarbonyloxybiphenol, a halogen-substituted alkenyloxybiphenol or a halogen-substituted alkoxyalkyloxybiphenol.

Further, derivatives represented by the general formula (1) wherein A represents phenyloxymethylphenyl can be synthesized in the same manner as that described above, except that instead of the 4'-octyloxybiphenol, use is made of a straight-chain or branched alkoxyphenyloxymethylphenol comprising an alkoxy group having 1 to 18 carbon atoms, an alkoxyalkyloxyphenyloxymethylphenol comprising an alkyl group having 1 to 18 carbon atoms and an alkoxy group having 1 to 3 carbon atoms, a straight-chain or branched alkenyloxyphenyloxymethylphenol comprising an alkenyl group having 2 to 18 carbon atoms, a straight-chain or branched alkylphenyloxymethylphenol comprising an alkyl group having 1 to 18 carbon atoms, an alkoxyalkylphenyloxymethylphenol compriing alkyl group having 1 to 18 carbon atoms and an alkoxy group having 1 to 3 carbon atoms, a straight-chain or branched alkenylphenyloxymethylphenol comprising an alkenyl group having 2 to 18 carbon atoms, a straight-chain or branched alkoxycarbonylphenyloxymethylphenol comprising an alkoxy group having 1 to 18 carbon atoms, an alkoxyalkyloxycarbonylphenyloxymethylphenol comprising alkyl group having 1 to 18 carbon atoms and an alkoxy group having 1 to 3 carbon atoms, a straight-chain or branched alkenyloxycarbonylphenyloxymethylphenol comprising an alkenyl group having 2 to 18 carbon atoms, a straight-chain or branched alkylcarbonyloxyphenyloxymethylphenol comprising an alkyl group having 1 to 18 carbon atoms, an alkoxyalkylcarbonyloxyphenyloxymethylphenol comprising an alkyl group having 1 to 18 carbon atoms and an alkoxy group having 1 to 3 carbon atoms, a straight-chain or branched alkenylcarbonyloxyphenyloxymethylphenol comprising an alkenyl group having 2 to 18 carbon atoms, a halogen-substituted alkoxyphenyloxymethylphenol, a halogen-substituted alkoxycarbonylphenylmethylphenol, a halogen-substituted alkenyloxyphenyloxymethylphenol or a halogen-substituted alkoxyalkyloxyphenyloxymethylphenol.

Further, derivatives represented by the general formula (1) wherein A represents benzyloxyphenyl, phenylcarbonyloxyphenyl or phenyloxycarbonylphenyl can be synthesized through the sue of a benzyloxyphenol derivative, a phenylcarbonyloxyphenol derivative or a phenyloxycarbonylphenol derivative instead of the above-described phenyloxymethylphenol derivative which is an alternative to the 4'-octyloxybiphenol.

EXAMPLE 3

Synthesis of (S)-2-(4'-octyloxybiphenyl-4-methyleneoxy)-5,5-dimethyl-δ-valerolactone First, 0.2 g of (S)-2-hydroxy-5,5-dimethyl-δ-valerolactone prepared in Example 1 was reacted with 0.5 g of 4'-octyloxy-4-bromomethylbiphenyl in the presence of a 0.06 g of 60% sodium hydride as a catalyst in dimethylformamide. The resultant reaction mixture was treated with dilute hydrochloric acid, the reaction product was extracted with diethyl ether, the extract was washed with water and dried over magnesium sulfate, the ether was removed from the dried solution to obtain a crude product, and the crude product was purified by a silica gel column chromatography to obtain 0.2 g of (S)-2-(4'-octyloxybiphenyl-4-methyleneoxy)-5,5-dimethyl-δ-valerolactone.

The purified product exhibited the following phase transition behavior.

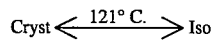

Derivatives represented by the general formula (1) wherein both the two $R_2$'s represent either a hydrogen atom or an alkyl group having 2 to 18 carbon atoms can be synthesized in the same manner as that described above, except that instead of the (S)-2-hydroxy-5,5-dimethyl-δ-valerolactone, use is made of (S)-2-hydroxy-δ-valerolactone or (S)-2-hydroxy-5,5-dialkyl-δ-valerolactone having 2 to 12 carbon atoms in the alkyl portion.

Further, derivatives represented by the general formula (1) wherein $R_1$ represents a straight-chain or branched alkyl group or alkenyl group, an alkoxyalkyl group comprising an alkyl group having 1 to 18 carbon atoms and an alkoxy group having 1 to 3 carbon atoms or the above-described groups substituted with a halogen, X represents an ether linkage, a direct bond, a carbonyloxy group or an oxycarbonyl group, A represents a biphenyl and Y represents a carbonyloxy group can be synthesized in the same manner as that described above, except that instead of the 4'-octyloxy-4-bromomethylbiphenyl, use is made of one wherein the octyloxy group portion of the 4'-octyloxy-4-bromomethylbiphenyl is replaced by a straight-chain alkoxy group having 1 to 7 or 9 to 18 carbon atoms, a branched alkoxy group having 3 to 18 carbon atoms, an alkoxyalkyloxy group comprising an alkyl group having 1 to 18 carbon atoms and an alkoxy group having 1 to 3 carbon atoms, a straight-chain or branched alkenyloxy group having 2 to 18 carbon atoms, a straight-chain or branched alkyl group having 1 to 18 carbon atoms, a straight-chain or branched alkenyl group having 2 to 18 carbon atoms, an alkoxyalkyl group comprising an alkyl group having 1 to 18 carbon atoms and an alkoxy group having 1 to 3 carbon atoms, a straight-chain or branched alkoxycarbonyl group having 1 to 18 carbon atoms in the alkoxy portion, a straight-chain or branched alkenyloxycarbonyl group having 2 to 18 carbon atoms in the alkenyl portion, an alkoxyalkyloxycarbonyl group comprising an alkyl group having 1 to 18 carbon atoms and an alkoxy group having 1 to 3 carbon atoms, a straight-chain or branched alkylcarbonyloxy group having 1 to 18 carbon atoms in the alkyl portion, a straight-chain or branched alkenylcarbonyloxy group having 2 to 18 carbon atoms in the alkenyl portion, an alkoxyalkylcarbonyloxy group comprising an alkyl group having 1 to 18 carbon atoms and an alkoxy group having 1 to 3 carbon atoms, a halogen-substituted alkoxy group, a halogen-substituted alkyl group, a halogen-substituted alkoxycarbonyl group, a halogen-substituted alkylcarbonyloxy group, a halogen-substituted alkenyloxy group or a halogen-substituted alkoxyalkyloxy group.

Further, derivatives represented by the general formula (1) wherein A represents phenyloxymethylphenyl can be synthesized in the same manner as that described above, except that instead of the 4'-octyloxy-4-bromomethylbiphenyl, use is made of one wherein the biphenyl portion of the 4'-octyloxy-4-bromomethylbiphenyl is replaced by phenyloxymethyl phenyl.

Further, derivatives represented by the general formula (1) wherein A represents benzyloxyphenyl, phenylcarbonyloxyphenyl or phenyloxycarbonylphenyl can be synthesized in the same manner as that described above, except that instead of the 4'-octyloxy-4-bromomethylbiphenyl, use is made of one wherein the biphenyl portion of the 4'-octyloxy-4-bromomethylbiphenyl is replaced by benzyloxyphenyl, phenylcarbonyloxyphenyl or phenyloxycarbonylphenyl.

Further, derivatives represented by the general formula (1) wherein A represents a group comprising phenylene and a pyrimidinylene or pyridazinylene group bonded thereto directly or through a carbonyloxy, oxycarbonyl, methyleneoxy or oxymethylene group can be synthesized in the same manner as that of the above-described Examples 1 to 3, except that instead of the 4'-octyloxybiphenyl-4-carboxylic acid, 4'-octyloxybiphenol or 4'-octyloxy-4-bromomethylbiphenyl group, use is made of one wherein one of the phenylenes in the biphenyl is a pyrimidinylene or pyridazinylene group, one wherein one of the phenylenes in the phenoxycarbonyloxyphenyl group is a pyrimidinylene or pyridazinylene group, one wherein one of the phenylenes in the phenylcarbonyloxyphenyl group is a pyrimidinylene or pyridazinylene group, one wherein one of the phenylenes in the benzyloxyphenyl group is a pyrimidinylene or pyridazinylene group, or one wherein one of the phenylenes in the phenoxymethylphenyl group is a pyridmidinylene or pyridazinylene group.

EXAMPLE 4

Synthesis of (S)-2,2-dimethyl-5-[4'-(5"-octyloxy-2"-pyrimidyl)-phenoxymethyl]valerolactone

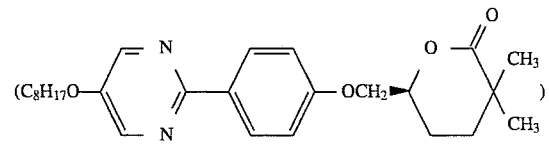

In 10 ml of anhydrous benzene were dissolved 1 g of (S)-2,2-dimethyl-5-hydroxymethyl-valerolactone synthesized in Referential Example 2, 1.9 g of 2-(4'-hydroxyphenyl)-5-octyloxypyrimidine, 1.7 g of triphenylphosphine and 1.1 g of azodicarboxylic acid, the solution was stirred for 12 hr, the solvent was removed from the solution by distillation, and the resultant residue was purified by a silica gel column chromatography through the use of hexane-ethyl acetate as a developing solvent and then recrystallized from a mixed solution comprising hexane and ethanol to obtain 1.1 g of (S)-2,2-dimethyl-5-[4'-(5"-octyloxy-2"-pyrimidinyl)phenoxymethyl]valerolactone (melting point: 141° C.).

A derivative represented by the general formula (2) wherein the two $R_2$'s are both an alkyl group having 2 to 18 carbon atoms can be synthesized in the same manner as that described above, except that instead of the (S)-2,2-dimethyl-5-hydroxymethyl-valerolactone, use is made of (S)-2,2-dialkyl-5-hydroxymethyl-valerolactone comprising alkyl groups each having 2 to 18 carbon atoms. Further, derivatives represented by the general formula (2) wherein $R_1$ represents a straight-chain or branched alkyl group or alkenyl group, an alkoxyalkyl group or the above-described groups substituted with a halogen, X represents a direct bond, an ether bond, a carbonyloxy group or an oxycarbonyl group, A represents phenylpyrimidine and Z represents an oxymethylene group can be synthesized in the same manner as that described above, except that instead of the 2-(4'-hydroxyphenyl)-5-octyloxypyrimidine, use is made of 2-(4'-hydroxyphenyl)-5-alkyloxypyrimidine wherein the alkyl group is a straight-chain alkyl group having 1 to 7 or 9 to 18 carbon atoms, 2-(4'-hydroxyphenyl)-5-alkyloxypyrimidine wherein the alkyl group is a branched alkyl group having 3 to 18 carbon atoms, 2-(4'-hydroxyphenyl)-5-alkoxyalkyloxypyrimidine wherein the alkoxy group and the alkyl group have 1 to 3 carbon atoms and 1 to 18 carbon atoms, respectively, 2-(4'-hydroxyphenyl)-5-alkenyloxypyrimidine wherein the alkenyl group is a straight-chain or branched alkenyl group having 2 to 18 carbon atoms, 2-(4'-hydroxyphenyl)-5-alkylpyrimidine wherein the alkyl group is a straight-chain or branched alkyl group having 1 to 18 carbon atoms, 2-(4'-hydroxyphenyl)-5-alkenylpyrimidine wherein the alkenyl group is a straight-chain or branched one having 2 to 18 carbon atoms, 2-(4'-hydroxyphenyl)-5-alkoxyalkylpyrimidine wherein the alkoxy group and the alkyl group have 1 to 3 carbon atoms and 1 to 18 carbon atoms, respectively, 2-(4'-hydroxyphenyl)-5-alkoxycarbonylpyrimidine wherein the alkoxy group is a straight-chain or branched alkoxy group having 1 to 18 carbon atoms, 2-(4'-hydroxyphenyl)-5-alkenyloxycarbonylpyrimidine wherein the alkenyl group is a straight-chain or branched alkenyl group having 2 to 18 carbon atoms, 2-(4'-hydroxyphenyl)-5-alkoxyalkyloxycarbonylpyrimidine wherein the alkoxy group and the alkyl group have 1 to 3 carbon atoms and 1 to 18 carbon atoms, respectively, 2-(4'-hydroxyphenyl)-5-alkylcarbonyloxypyrimidine wherein the alkyl group is a straight-chain or branched alkyl group having 1 to 18 carbon atoms, 2-(4'-hydroxyphenyl)-5-alkenylcarbonyloxypyrimidine wherein the alkenyl group is a straight-chain or branched alkenyl group having 2 to 18 carbon atoms, 2-(4'-hydroxyphenyl)-5-alkoxyalkylcarbonyloxypyrimidine wherein the alkoxy group and the alkyl group have 1 to 3 carbon atoms and 1 to 18 carbon atoms, respectively, or the above-described compounds wherein part of the hydrogen atoms in the alkyl group, alkoxy group or alkenyl group are substituted with a halogen.

Further, a series of derivatives wherein A corresponds to the followings can be synthesized in the same manner as that described above, except that instead of the 2-(4'-hydroxyphenyl)-5-octyloxypyrimidine or the above-described compounds as an alternative thereto, use is made of one wherein the phenylpyrimidine skeleton is replaced by a phenylpyridine, phenylpyridazine, phenylpyrazine, phenyloxycarbonylpyridine, phenyloxycarbonylpyridazine, benzoyloxypyridine, benzoyloxypyridazine, benzyloxypyridine or benzyloxypyridazine skeleton, or a skeleton wherein the position of the phenyl group and the position of the pyrimidine, pyridine, pyridazine or pyrazine group are replaced with each other.

Further, derivatives represented by the general formula (2) wherein Y represents an oxycarbonyl group can be synthesized in the same manner as that described above, except that instead of the (S)-2,2-dimethyl-5-hydroxymethyl-valerolactone, use is made of (S)-2,2-dialkyl-5-hydroxycarbonyl-valerolactone having 1 to 18 carbon atoms in the alkyl portion.

EXAMPLE 5

Synthesis of (S)-2,2-dimethyl-5-[4"-octyloxy-4'-biphenyloxymethyl)-valerolactone

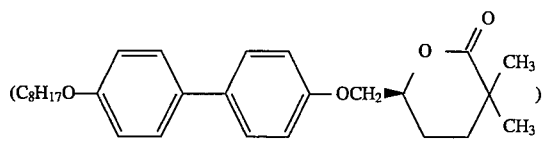

(S)-2,2-dimethyl-5-(4"-octyloxy-4'-biphenyloxymethyl)-valerolactone (melting point: 112° C.) was prepared in the same manner as that of Example 4, except that instead of the 2-(4'-hydroxyphenyl)-5-octyloxypyrimidine, use was made of 4'-octyloxy-4-biphenol in the same equivalent amount.

Derivatives represented by the general formula (2) wherein the two $R_2$'s are both an alkyl group having 2 to 18 carbon atoms can be synthesized in the same manner as that described above, except that instead of the (S)-2,2-dimethyl-5-hydroxymethyl-valerolactone, use is made of (S)-2,2-dialkyl-5-hydroxymethyl-valerolactone having 2 to 12 carbon atoms in the alkyl portion. Further, derivatives represented by the general formula (2) wherein $R_1$ represents a straight-chain or branched alkyl group or alkenyl group, alkoxyalkyl group or the above-described groups substituted with a halogen, X represents a direct bond, an ether bond, a carbonyloxy group or an oxycarbonyl group, A represents biphenylene and Z represents an oxymethylene group can be synthesized in the same manner as that described above, except that instead of the 4'-octyloxy-4-biphenol, use is made of 4'-alkyloxy-4-biphenol wherein the alkyl group is a straight-chain alkyl group having 1 to 7 or 9 to 18 carbon atoms, 4'-alkyloxy-4-biphenol wherein the alkyl group is a branched alkyl group having 3 to 18 carbon atoms, 4'-(alkoxyalkyloxy)-4-biphenol wherein the alkoxy group and the alkyl group have 1 to 3 carbon atoms and 1 to 18 carbon atoms, respectively, 4'-alkenyloxy-4-biphenol wherein the alkenyl group is a straight-chain or branched alkenyl group having 2 to 18 carbon atoms, 4'-alkyl-4-biphenol wherein the alkyl group is a straight-chain or branched alkyl group having 1 to 18 carbon atoms, 4'-alkenyl-4-biphenol wherein the alkenyl group is a straight-chain or branched one having 2 to 18 carbon atoms, 4-(alkoxyalkyl)-4-biphenol wherein the alkoxy group and the alkyl group have 1 to 3 carbon atoms and 1 to 18 carbon atoms, respectively, 4'-(alkoxycarbonyl)-4-biphenol wherein the alkoxy group is a straight-chain or branched alkoxy group having 1 to 18 carbon atoms, 4'-(alkenyloxycarbonyl)-4-biphenol wherein the alkenyl group is a straight-chain or branched alkenyl group having 2 to 18 carbon atoms, 4'-alkoxyalkyloxycarbonyl)-4-biphenol wherein the alkoxy group and the alkyl group have 1 to 3 carbon atoms and 1 to 18 carbon atoms, respectively, 4'-(alkylcarbonyloxy)-4-biphenol wherein the alkenyl group is a straight-chain or branched alkyl group having 1 to 18 carbon atoms, 4'-(alkenylcarbonyloxy)-4-biphenol wherein the alkenyl group is a straight-chain or branched alkenyl group having 2 to 18 carbon atoms, 4'-(alkoxyalkylcarbonyloxy)-4-biphenol wherein the alkoxy group and the alkyl group have 1 to 3 carbon atoms and 1 to 18 carbon atoms, respectively, or the above-described compounds wherein part of the hydrogen atoms in the alkyl group, alkoxy group or alkenyl group are substituted with a halogen.

Further, a series of derivatives wherein A corresponds to the following can be synthesized in the same manner as that described above, except that instead of the 4'-octyloxy-4-biphenol or the above-described compounds as an alternative thereto, use is made of one wherein the biphenylene skeleton is replaced by a benzoyloxyphenyl, phenyloxycarbonylphenyl, benzyloxyphenyl or phenoxymethylphenyl skeleton, or a skeleton wherein a halogen, such as fluorine, has been introduced into the phenyl group of the above-described skeleton.

Further, a derivative represented by the general formula (2) wherein Y represents an oxycarbonyl group can be synthesized in the same manner as that described above, except that instead of the (S)-2,2-dimethyl-5-hydroxymethyl-valerolactone, use is made of (S)-2,2-dialkyl-5-hydroxycarbonyl-valerolactone having 1 to 12 carbon atoms in the alkyl portion.

EXAMPLE 6

Synthesis of
(S)-5-[4'-(5''-octyloxy-2''-pyrimidyl)-phenoxymethyl]-valerolactone

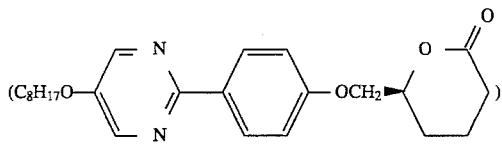

(S)-5-[4'-(5''-octyloxy-2''-pyrimidyl)-phenoxymethyl] valerolactone (melting point: 130° C.) was prepared in the same manner as that of Example 4, except that (S)-5-hydroxymethyl-valerolactone synthesized in Referential Example 3 was used in a half equivalent instead of the (S)-2,2-dimethyl-5-hydroxymethyl-valerolactone and the other compounds were each used in a half amount of that used in Example 4.

Derivatives represented by the general formula (2) wherein $R_1$ represents a straight-chain or branched alkyl group or alkenyl group, alkoxyalkyl group or the above-described groups substituted with a halogen, X represents a direct bond, an ether bond, a carbonyloxy group or an oxycarbonyl group, A represents phenylpyrimidine and Z represents an oxymethylene group can be synthesized in the same manner as that described above, except that instead of the 2-(4'-hydroxyphenyl)-5-octyloxypyrimidine, use is made of 2-(4'-hydroxyphenyl)-5-alkyloxypyrimidine wherein the alkyl group is a straight-chain alkyl group having 1 to 7 carbon atoms or 9 to 18 carbon atoms, 2-(4'-hydroxyphenyl)-5-alkyloxypyrimidine wherein the alkyl group is a branched alkyl group having 3 to 18 carbon atoms, 2-(4'-hydroxyphenyl)-5-alkoxyalkyloxypyrimidine wherein the alkoxy group and the alkyl group have 1 to 3 carbon atoms and 1 to 18 carbon atoms, respectively, 2-(4'-hydroxyphenyl)-5-alkenyloxypyrimidine wherein the alkenyl group is a straight-chain or branched alkenyl group having 2 to 18 carbon atoms, 2-(4'-hydroxyphenyl)-5-alkylpyrimidine wherein the alkyl group is a straight-chain or branched alkyl group having 1 to 18 carbon atoms, 2-(4'-hydroxyphenyl)-5-alkenylpyrimidine wherein the alkenyl group is a straight-chain or branched one having 2 to 18 carbon atoms, 2-(4'-hydroxyphenyl)-5-alkoxyalkylpyrimidine wherein the alkoxy group and the alkyl group have 1 to 3 carbon atoms and 1 to 18 carbon atoms, respectively, 2-(4'-hydroxyphenyl)-5-alkoxycarbonylpyrimidine wherein the alkoxy group is a straight-chain or branched alkoxy group having 1 to 18 carbon atoms, 2-(4'-hydroxyphenyl)-5-alkenyloxycarbonylpyrimidine wherein the alkenyl group is a straight-chain or branched alkenyl group having 2 to 18 carbon atoms, 2-(4'-hydroxyphenyl)-5-alkoxyalkyloxycarbonylpyrimidine wherein the alkoxy group and the alkyl group have 1 to 3 carbon atoms and 1 to 18 carbon atoms, respectively, 2-(4'-hydroxyphenyl)-5-alkylcarbonyloxypyrimidine wherein the alkyl group is a straight-chain or branched alkyl group having 1 to 18 carbon atoms, 2-(4'-hydroxyphenyl)-5-alkenylcarbonyloxypyrimidine wherein the alkenyl group is a straight-chain or branched alkenyl group having 2 to 18 carbon atoms, 2-(4'-hydroxyphenyl)-5-alkoxyalkylcarbonyloxypyrimidine wherein the alkoxy group and the alkyl group have 1 to 3 carbon atoms and 1 to 18 carbon atoms, respectively, or the above-described compounds wherein part of the hydrogen atoms in the alkyl group, alkoxy group or alkenyl group are substituted with a halogen.

Further, a series of derivatives wherein A corresponds to the following can be synthesized in the same manner as that described above, except that instead of the 2-(4'-hydroxyphenyl)-5-octyloxypyrimidine or the above-described compounds as an alternative thereto, use is made of one wherein the phenylpyrimidine skeleton is replaced by a phenylpyridine, phenylpyridazine, phenylpyrazine, phenyloxycarbonylpyridine, phenyloxycarbonylpyridazine, benzoyloxypyridine, benzoyloxypyridazine, benzyloxypyridine or benzyloxypyridazine skeleton, or a skeleton wherein the position of the phenyl group and the position of the pyrimidine, pyridine, pyridazine or pyrazine group are replaced with each other.

Further, a derivative represented by the general formula (2) wherein Y represents an oxycarbonyl group can be synthesized in the same manner as that described above, except that instead of the (S)-5-hydroxymethyl-valerolactone, use is made of (S)-5-hydroxycarbonyl-valerolactone.

Further, a series of derivatives wherein A corresponds to the following can be synthesized in the same manner as that described above, except that instead of the 2-(4'-hydroxyphenyl)-5-octyloxypyrimidine or the above-described compounds as an alternative thereto, use is made of one wherein the phenylpyrimidine skeleton is replaced by a biphenylene, benzoyloxyphenyl, phenyloxycarbonylphenyl, benzyloxyphenyl or phenyloxymethylphenyl skeleton, or a skeleton wherein a halogen, such as fluorine, has been introduced into the phenyl group of the above-described skeleton.

EXAMPLE 7

Synthesis of
(S)-2-(4'-octyloxybiphenyl-4-carboxy]-5,5-dimethyl-δ-valerolactone

In 100 ml of THF was dissolved 5 g (27 mmol) of tert-butyl (S)-γ-butyrolactonecarboxylate. The solution was purged with argon and cooled on a dry ice-acetone bath, and 27 ml (3 equivalents) of 3M methyl magnesium bromide-ether solution was slowly dropwise added thereto. After the completion of the addition, the mixture was stirred at the same temperature for 2 hr for a reaction. Then, water was slowly dropwise added thereto, the mixture was neutralized with 3N HCl, THF was removed by distillation under reduced pressure, and the residue was extracted with ethyl acetate, and the extract was washed with dilute hydrochloric acid and then a saturated saline solution and dried over magnesium sulfate. The solvent was removed from the dried solution, and the residue was purified by a silica gel column chromatography to obtain 1.45 g of t-butyl (S)-2,5-dihydroxy-5-methyl-hexanoate.

The product was dissolved in 50 ml of benzene, p-toluenesulfonic acid was added thereto, the mixture was refluxed for 5 hr, and the resultant reaction product was purified by a column chromatography to obtain 0.7 g of (S)-2-hydroxy-5,5-dimethyl-δ-valerolactone.

Thereafter, 0.1 g of the product and 0.2 g of 4'-octyloxybiphenyl-4-carboxylic acid were dissolved in methylene chloride, 0.2 g of dicyclohexylcarbodiimide (DCC) and 0.05 g of dimethylaminopyridine were added thereto, and the mixture was allowed to react with each other at room temperature overnight. The reaction mixture was filtered, and the filtrate was concentrated and purified by a column chromatography to obtain 0.18 g of (S)-2-(4'-octyloxybiphenyl-4-carboxy)-5,5-dimethyl-δ-valerolactone. This product had a melting point of 128° C.

EXAMPLE 8

Synthesis of
(S)-2-(4'-octyloxybiphenyl-4-carboxy)-5,5-dimethyl-δ-valerolactone 6,3 g of tert-butyl (S)-2,5-dihydroxy-5-ethylhexanoate was prepared in the same manner as that of Example 7, except that a Grignard reagent was prepared in 200 ml of THF from 5.16 g of magnesium and 29.3 g of ethyl bromide and then added in an argon gas stream to a solution of 10 g of tert-butyl (S)-γ-butyrolactone-γ-carboxylate dissolved in 100 ml of THF while cooling on dry ice.

The product was dissolved in 150 ml of benzene, 0.2 g of p-toluenesulfonic acid was added thereto, the mixture was refluxed for 5 hr, and the resultant reaction product was purified by a column chromatography to obtain 4.7 g of (S)-2-hydroxy-5,5-diethyl-δ-valerolactone. 0.19 g of (S)-2-(4'-octyloxybiphenyl-4-carboxy)-5,5-diethyl-δ-valerolactone was prepared in the same manner as that of Example 7, except that use was made of 0.1 g of the product purified above. The resultant product had a melting point of 81.2° C.

EXAMPLE 9

3.2 g of (S)-2-hydroxy-5,5-dipropyl-δ-valerolactone was prepared in the same manner as that of Example 8, except that 33 g of propyl bromide was used instead of ethyl bromide. 0.15 g of (S)-2-(4'-octyloxybiphenyl-4-carboxy)-5,5-dipropyl-δ-valerolactone was prepared in the same manner as that of Example 7, except that use was made of 0.1 g of the product prepared above. The resultant product had a melting point of 65.9° C.

EXAMPLE 10

0.9 g of (S)-2-hydroxy-5,5-dihexyl-δ-valerolactone was prepared in the same manner as that of Example 8, except that 11.4 g of hexyl bromide was used instead of ethyl bromide. 0.13 g of (S)-2-(4'-octyloxybiphenyl-4-carboxy)-5,5-dihexyl-δ-valerolactone was prepared in the same manner as that of Example 2, except that use was made of 0.1 g of the product prepared above. The resultant product had a melting point of 83° C.

$^1$HNMR=8.10 (2HD), 7.59 (4Hg), 6.95 (2Hd), 5.46 (1Ht), 4.0 (2Ht), 1.1–2.4 (36Hm), 0.90 (9Ht)

EXAMPLE 11

1 g of (S)-2-hydroxy-5,5-didecyl-δ-valerolactone was prepared in the same manner as that of Example 8, except that 15 g of decyl bromide was used instead of ethyl bromide. 0.1 g of (S)-2-(4'-octyloxybiphenyl-4-carboxy)-5,5-didecyl-δ-valerolactone was prepared in the same manner as that of Example 7, except that use the was made of 0.1 g of the product prepared above. The resultant product had a melting point of 66.2° C.

$^1$HNMR=8.10 (2HD), 7.56 (4Hg), 6.95 (2Hd), 5.45 (1Ht), 4.0 (2Ht), 1.1–2.4 (52Hm), 0.90 (9Ht)

EXAMPLE 12

0.1 g of 2-hydroxy-5,5-diethyl-δ-valerolactone prepared in Example 8 and 0.2 g of 4'-octyloxy-3'-fluorobiphenyl-4-carboxylic acid were dissolved in dried benzene, 0.1 g of diethyl azodicarboxylate and 0.2 g of triphenyphoxphine were added thereto, and the mixture was allowed to react with each other at room temperature overnight. The solvent removed from the resultant solution by distillation, and the residue was purified by a column chromatography to obtain 0.12 g of (R)-2-(4'-octyloxy-3'-fluorobiphenyl-4-carboxy)-5,5-diethyl-δ-valerolactone. This product had a melting point of 74° C.

EXAMPLE 13

0.1 g 2-hydroxy-5,5-diethyl-δ-valerolactone prepared in Example 8 was reacted with 0.2 g of 2-(4-carboxyphenyl)-5-decyloxypyrimidine in the same manner that of Example 7, and the reaction mixture was purified by a silica gel chromatography to obtain 0.07 g of (S)-2-(5-decyloxy-2-pyrimidinophenyl-4-carboxy)-5,5-diethyl-δ-valerolactone. This product has a melting point of 98° C.

EXAMPLE 14

0.06 g of (R)-2-(5-octyloxy-2-pyrimidinophenyl-4-oxy)-5,5-diethyl-δ-valerolactone was prepared in the same manner as that of Example 12, except that 4'-octyloxy-3'-fluorobiphenyl-4-carboxylic acid was replaced with the same amount of 2-(4-hydroxyphenyl)-5-octyloxy-pyrimidine. This product has a melting point of 95° C.

EXAMPLE 15

0.15 g of (R)-2-(4-octyloxy-3-cyanophenylcarboxy)-5,5-diethyl-δ-valerolactone was prepared in the same manner as that of Example 12, except that 0.3 g of 4-octyloxy-3-cyanobenzoic acid was used instead of 0.2 g of 4'-octyloxy-3'-fluorobiphenyl-4-carboxylic acid. The compound thus prepared was oleaginous at room temperature.

EXAMPLE 16

Synthesis of
(S)-2,2-diethyl-5-[4'-(5"-octyloxy-2"-pyrimidyl)-phenoxymethyl]valerolactone

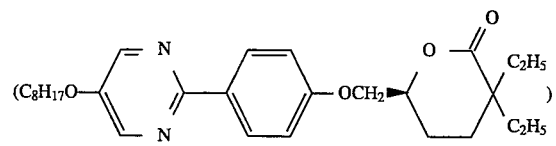

A reaction was conducted in the same manner as that of Reference Example 2, except that 1.7 g of n-butanoic acid was used instead of 5 g of isobutyric acid, thereby obtaining 1.1 g of (5S)-2-ethyl-5-hydroxymethyl-valerolactone. 0.5 g of the reaction product, 0.95 g of 2-(4'-hydroxyphenyl)-5-octyloxypyrimidine, 0.85 g of triphenylphosphine and 0.6 g of diethyl azodicarboxylate were dispersed in 10 ml of anhydrous benzene, the dispersion was stirred for 12 hr, the solvent was removed from the resultant solution by distillation, and the resultant residue purified by a silica gel chromatography through the use of hexane-ethyl acetate as a developing solvent and then recrystallized from a mixed solution comprising hexane and ethanol to obtain 0.9 g of (5S)-2-ethyl-5-[4'-(5''-octyloxy-2''-pyrimidyl)-phenoxymethyl]valerolactone.

1.77 ml of a solution (1.66 mol/liter) of n-butyllithium in hexane was dropwise added at 0° C. to a mixed solution comprising 0.33 g of disopropylamine and 6 ml of anhydrous THF, the solution was cooled to −78° C., 1.6 g of iodethane was dropwise added thereto, and the mixture was stirred for 2 hr. 10 ml of water was added to the reaction mixture, the mixture was extracted with methylene chloride, the extract was washed with a saturated saline solution and dehydrated over magnesium sulfate, the solvent was removed by distillation, and the resultant residue was purified by a silica gel chromatography through the use of hexane-ethyl acetate as a developing solvent to obtain 0.18 g of (S)-2,2-diethyl-5-[4'-5''-octyloxy-2''-pyrimidyl)-phenoxymethyl]valerolactone (melting point: 101° C.).

EXAMPLE 17

Synthesis of
(S)-2,2-dimethyl-5-[(4'-(5''-octyl-2''-pyrimidyl)-2''-fluorophenoxymethyl] valerolactone

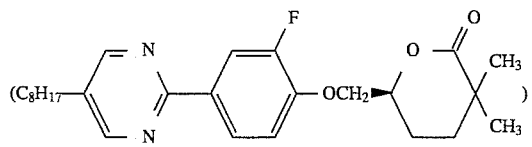

An intended product (melting point: 81° C.) was prepared in the same manner as that of Example 16, except that 2-(4'-hydroxyphenyl)-5-octyloxypyrimidine was replaced with the same equivalent of 2-(3'-fluoro-4'-hydroxyphenyl)-5-oxtylpyrimidine.

EXAMPLE 18

Synthesis of
(S)-2,2-dimethyl-5-[4'-(5''-(4'''-octylphenyl)-2''-pyrimidyl)phenoxymethylvalerolactone

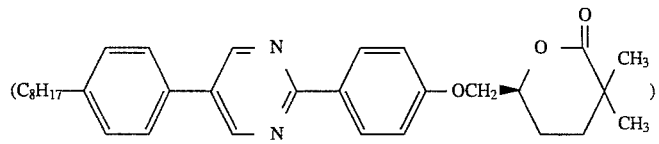

An intended product (melting point: 131° C., point of change to transparent 171° C.) was prepared in the same manner as that of Example 16, except that 2-(4'-hydroxyphenyl)-5-octyloxypyrimidine was replaced with the same equivalent of 2-(4'-hydroxyphenyl)-5-(4''-octylphenyl)pyrimidine.

EXAMPLE 19

Synthesis of
(S)-2,2-diethyl-5-(4'-(4''-decyloxyphenoxycarbonyl)-phenoxymethylvalerolactone

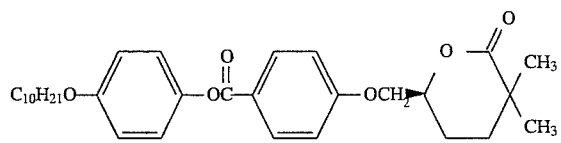

An intended product (melting point: 92° C.) was prepared in the same manner as that of Example 16, except that 2-(4'-hydroxyphenyl)-5-octyloxypyrimidine was replaced with the same equivalent of 4-(4'-decyloxyphenoxycarbonyl)phenol.

EXAMPLE 20

0.07 g of (S)-2-[4-(3-chloro-4-octyloxibenzoyloxy]-5,5-dipropyl-δ-valerolactone was prepared in the same manner as that of Example 9, except that 4-(3-chloro-4-octyloxybenzoyloxy) benzoic acid was used instead of 4'-octyloxybiphenyl-4-carboxylic acid without change of the amount thereof. The compound thus prepared was oleaginous at room temperature.

EXAMPLE 21

0.09 g of (S)-2-[4-(4-octyloxyphenoxymethyl) benzoyloxy]-5,5-dipropyl-δ-valerolactone was prepared in the same manner as that of Example 9, except that 4-(4-octyloxyphenoxymethyl) benzoic acid was used instead of 4'-octyloxybiphenyl-4-carboxylic acid without change of the amount thereof. The compound thus prepared had a melting point of 65° C.

EXAMPLE 22

0.06 g of (S)-2-[6-(7-octyne-1-oxy)2-naphtoyloxy]-5,5-dipropyl-δ-valerolactone was prepared in the same manner as that of Example 9, except that 6-(7-octene-1-oxy) naphthalene-2-carboxylic acid was used instead of 4'-octyloxybiphenyl-4-carboxylic acid without change of the amount thereof. The compound thus prepared was oleaginous at room temperature.

EXAMPLE 23

0.1 g of 2-hydroxy-5,5-dipropyl-δ-valerolactone was reacted with 0.2 g of 6-(1H,1H,2H,2H-perfluorohexyloxy) in the same manner as that of Example 12 and the resultant product was refined by silica gel chromatography to obtain 0.08 g of (R)-2-[6-(1H,1H,2H, 2H- perfluoroxyhexyloxy)2-naphthoyloxy]-5,5-dipropyl-δ-valerolactone. The compound thus prepared was oleaginous at room temperature.

EXAMPLE 24

0.08 g of (S)-2-(4'-hexyloxybiphenyl-4-carboxy)-5,5-dipropyl-δ-valerolactone was prepared in the same manner as that of Example 9, except that 4'-hexyloxybiphenyl-4-carboxylic acid was used instead of 4'-octyloxybiphenyl-4-carbonic acid without change of the amount thereof. The compound thus prepared had a melting point of 109° C.

EXAMPLE 25

0.09 g of (S)-2-(4'-hexadesiloxybiphenyl-4-carboxy)-5,5-dipropyl-δ-valerolactone was prepared in the same manner as that of Example 9, except that 4'-hexadesiloxybiphenyl-4-carboxylic acid was used instead of 4'-octyloxybiphenyl-4-carboxylic acid without change of the amount thereof. The compound thus prepared had a melting point of 78° C.

EXAMPLE 26

0.08 g of (S)-2-[4-(1-methylheptyloxy)benzoyloxy]-5,5-dipropyl-δ-valerolactone was prepared in the same manner as that of Example 9, except that 4-(1-methylheptyloxy)benzoic acid was used instead of 4'-octyloxybiphenyl-4-carboxylic acid without change of the amount thereof. The compound thus prepared was oleageous at room temperature.

EXAMPLE 27

0.07 g of (S)-2-[4-(4-dodecyloxybenzoyloxy) benzoyloxy]-5,5-dipropyl-δ-valerolactone was prepared in the same manner as that of Example 9, except that 4-(4-dodecyloxybenzoyloxy)benzoic acid was used instead of 4'-octyloxybiphenyl-4-carboxylic acid without change of the amount thereof. The compound thus prepared had a melting point of 91° C.

EXAMPLE 28

0.09 g of (S)-2-(4'-hexadecyloxybiphenyl-4-carboxy)-5,5-didecyl-δ-valerolactone was prepared in the same manner as that of Example 11, except that 4'-hexadecyloxybiphenyl-4-carboxylic acid was used instead of 4'-octyloxybiphenyl-4-carboxylic acid without change of the amount thereof. The compound thus prepared had a melting point of 56° C.

EXAMPLE 29

0.08 g of (S)-2-[4'-hexyloxybiphenyl-4-carboxy)-5,5-didecyl-δ-valerolactone was prepared in the same manner as that of Example 11, except that 4'-hexyloxybiphenyl-4-carboxylic acid was used instead of 4'-octyloxybiphenyl-4-carboxylic acid without change of the amount thereof. The compound thus prepared had a melting point of 69° C.

EXAMPLE 30

The following compounds were mixed at the following mixing ratio to prepare a liquid crystal composition.

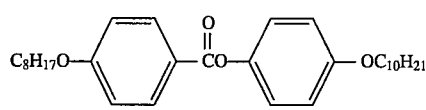 2 mol %

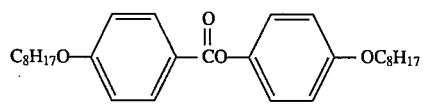 2 mol %

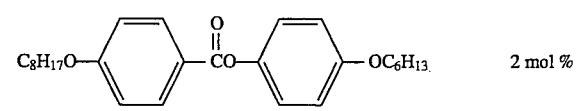 2 mol %

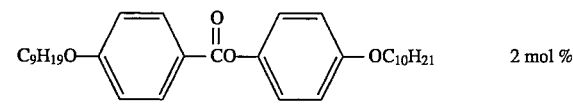 2 mol %

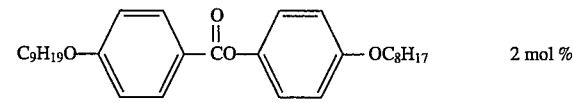 2 mol %

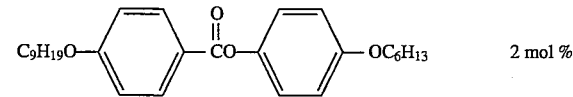 2 mol %

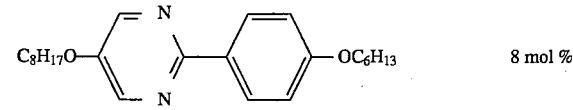 8 mol %

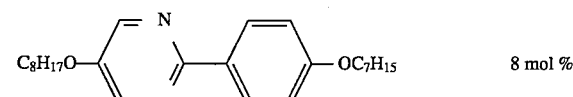 8 mol %

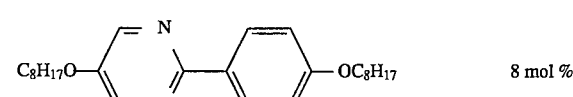 8 mol %

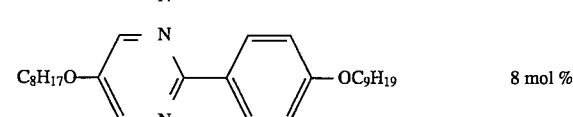 8 mol %

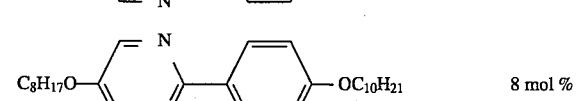 8 mol %

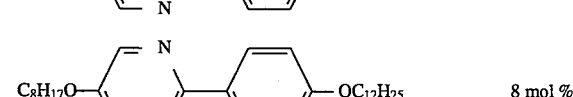 8 mol %

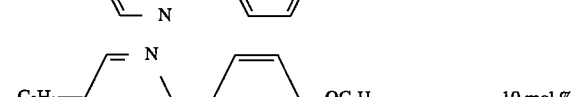 10 mol %

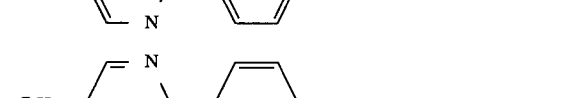 10 mol %

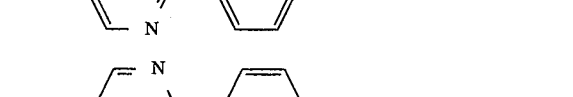 10 mol %

-continued

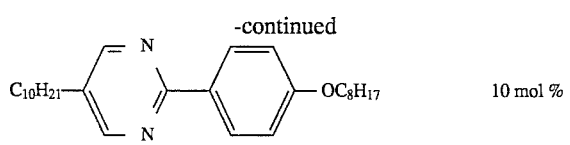                   10 mol %

This composition showed the following phase transition:

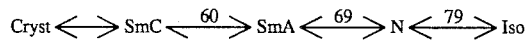

In the above expression, Cryst represents the crystal, SmC represents the smectic C phase, N represents the nematic phase, and each number given in the vicinity of the arrow shows the transition temperature (°C.) to the corresponding phase.

Since this liquid crystal composition consisted of non-chiral compounds alone, it was not a ferroelectric liquid crystal and showed no spontaneous polarization.

Then, 98% by mole of this composition was mixed with 2% by mole of the optically actively compound prepared in Example 1 to prepare a ferroelectric liquid crystal composition. This ferroelectric liquid crystal composition showed the Sm*C phase at temperatures from room temperature to 60° C., showed the SmA phase at 60° to 69° C., showed the chiral nematic phase at 69° to 77° C., and became an isotropic liquid at higher temperatures.

Separately, there was prepared a 2 μm-thick cell provided with a transparent electrode subjected to coating with a polyimide as an aligning agent and then a rubbing treatment for parallel alignment. The ferroelectric liquid crystal composition was injected into the cell to prepare a ferroelectric liquid crystal element. The liquid crystal element was arranged between two orthogonally crossing polarizers, and an electric field was applied thereto. The application of ±20 V caused the intensity of the transmitted light to be changed. The response time was determined from this change and found to be 90 μsec at 25° C.

EXAMPLE 31

Then 98% by mole of the liquid crystal composition consisting of non-chiral compounds alone used in Example 7 was mixed with 2% by mole of the optically active compound prepared in Example 4 to prepare a ferroelectric liquid crystal composition. This ferroelectric liquid crystal composition showed the Sm*C phase at temperatures from room temperature to 59° C., showed the SmA phase at 59° to 68° C., showed the chiral nematic phase at 68° to 78° C., and became an isotropic liquid at higher temperatures.

Separately, there was prepared a 2 μm-thick cell provided with a transparent electrode subjected to coating with a polyimide as an aligning agent and then a rubbing treatment for parallel alignment. The ferroelectric liquid crystal composition was injected into the cell to prepare a ferroelectric liquid crystal element. The liquid crystal element was arranged between two orthogonally crossing polarizers, and an electric field was applied thereto. The application of ±20 V caused the intensity of the transmitted light to be changed.

The response time was determined from this change and found to be 85 μsec at 25° C.

EXAMPLE 32

A liquid crystal composition consisting of the following non-chiral compounds was prepared.

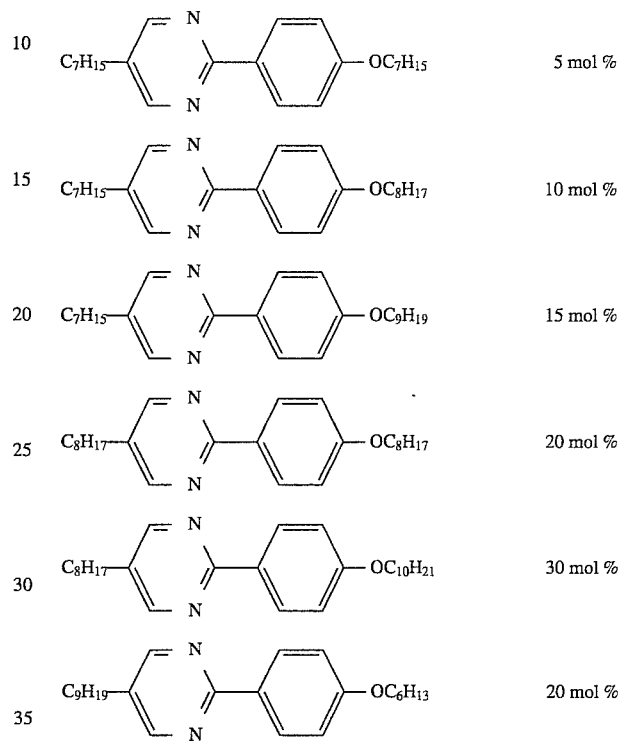

This liquid crystal composition consisting of non-chiral compounds shown the following phase transition:

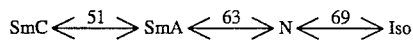

2% by mole of the following the compounds prepared in the above Examples were added to 98% by mole of the above composition to prepare ferromagnetic liquid crystal compositions.

Compound 1

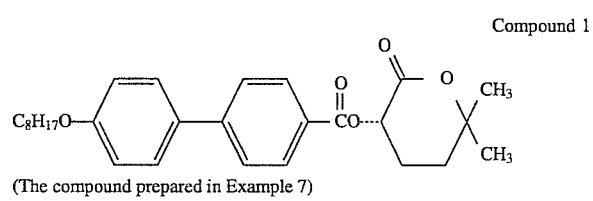

(The compound prepared in Example 7)

Compound 2
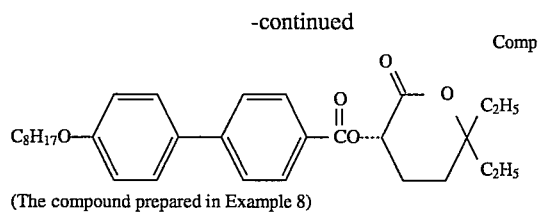
(The compound prepared in Example 8)

Compound 3
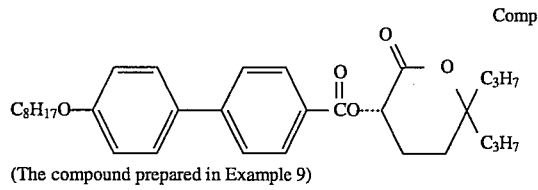
(The compound prepared in Example 9)

Compound 4
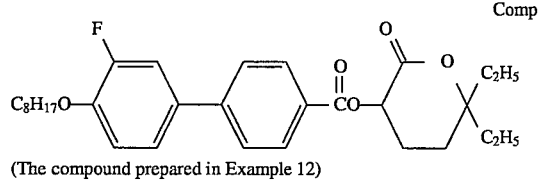
(The compound prepared in Example 12)

Compound 5
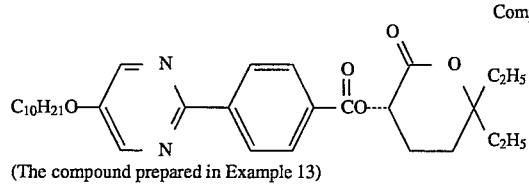
(The compound prepared in Example 13)

Compound 6
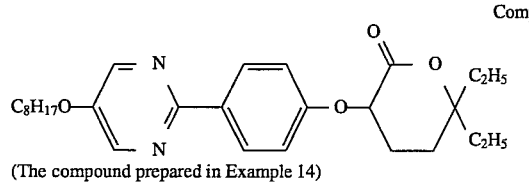
(The compound prepared in Example 14)

Compound 7
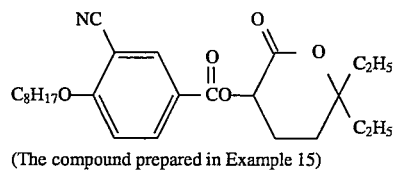
(The compound prepared in Example 15)

Compound 8
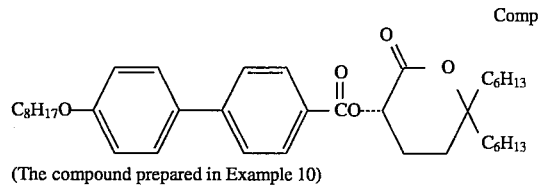
(The compound prepared in Example 10)

Compound 9
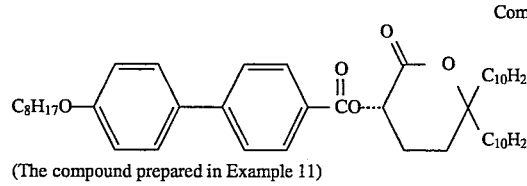
(The compound prepared in Example 11)

Compound 10
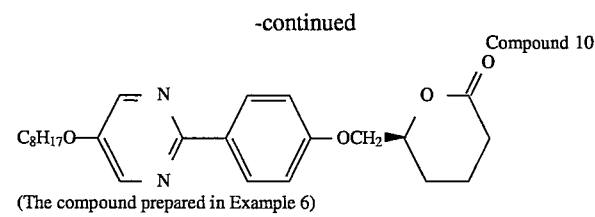
(The compound prepared in Example 6)

Compound 11
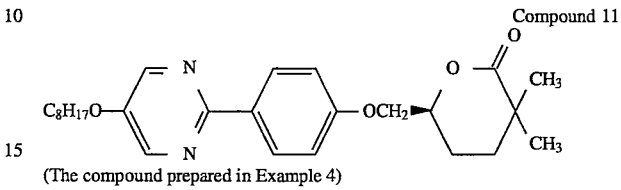
(The compound prepared in Example 4)

Compound 12
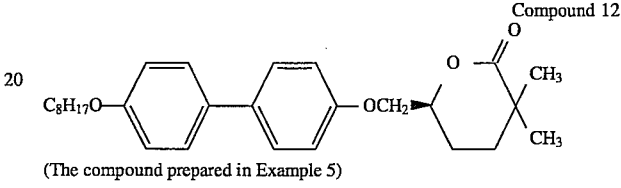
(The compound prepared in Example 5)

Compound 13
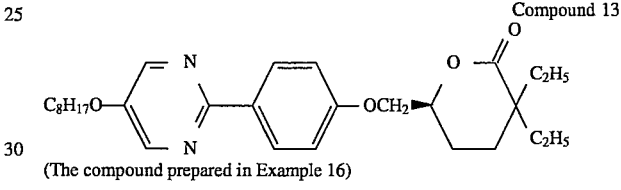
(The compound prepared in Example 16)

Compound 14
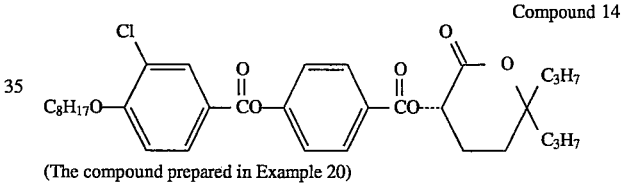
(The compound prepared in Example 20)

Compound 15
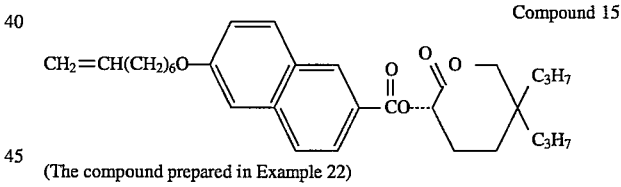
(The compound prepared in Example 22)

Compound 16
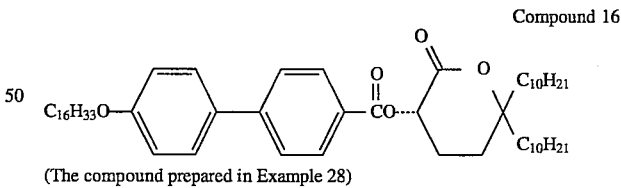
(The compound prepared in Example 28)

Compound 17
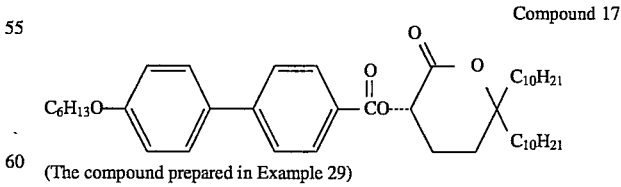
(The compound prepared in Example 29)

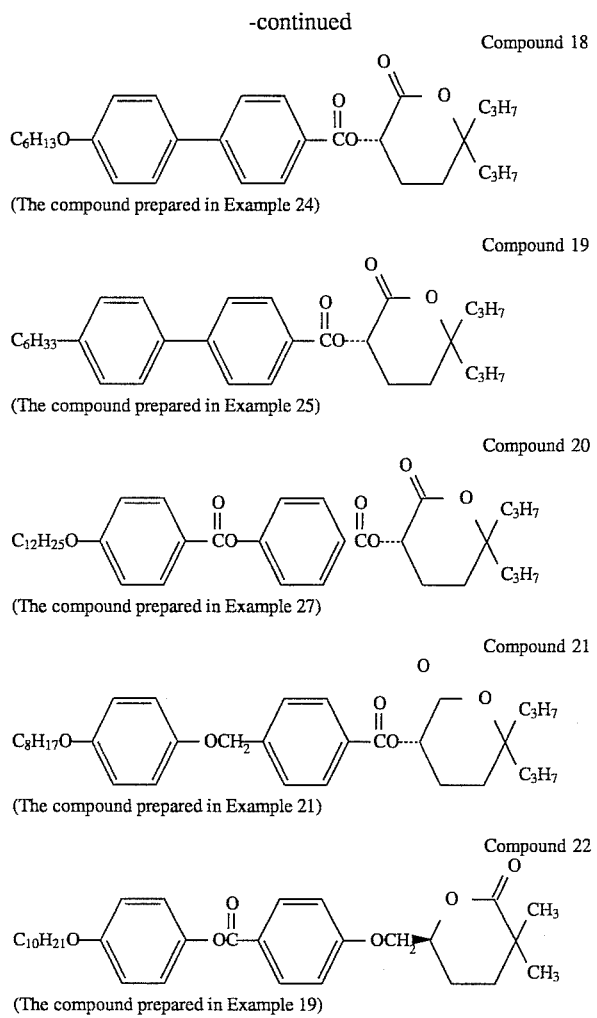
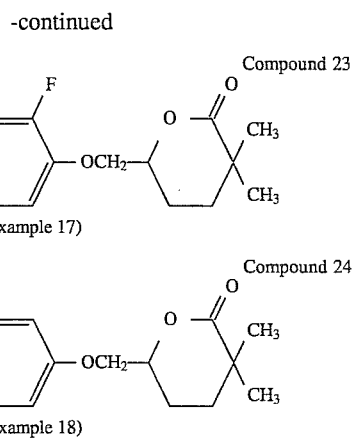

The thus obtained liquid crystal compositions were charged in a 8 μm cell and the spontaneous polarizations thereof at 25° C. were determined by the triangle wave method.

The spontaneous polarizations thus determined and the phase transition phenomena thereof are shown in Table 1.

TABLE 1

| Added compound | Phase transition temperature (°C.) | Spontaneous polarization nC/cm$^2$ |
|---|---|---|
| Compound 1 | SmC* ⇌52⇌ SmA ⇌59⇌ N* ⇌66⇌ Iso | −4.7 |
| Compound 2 | SmC* ⇌53⇌ SmA ⇌61⇌ N* ⇌66⇌ Iso | −5.7 |
| Compound 3 | SmC* ⇌52⇌ SmA ⇌59⇌ N* ⇌65⇌ Iso | −9.6 |
| Compound 4 | SmC* ⇌50⇌ SmA ⇌58⇌ N* ⇌65⇌ Iso | +9.7 |
| Compound 5 | SmC* ⇌51⇌ SmA ⇌59⇌ N* ⇌66⇌ Iso | −3.6 |
| Compound 6 | SmC* ⇌52⇌ SmA ⇌59⇌ N* ⇌65⇌ Iso | — |
| Compound 7 | SmC* ⇌50⇌ SmA ⇌60⇌ N* ⇌65⇌ Iso | +4.1 |
| Compound 8 | SmC* ⇌52⇌ SmA ⇌59⇌ N* ⇌65⇌ Iso | −11.3 |
| Compound 9 | SmC* ⇌50⇌ SmA ⇌57⇌ N* ⇌65⇌ Iso | −11.0 |

TABLE 1-continued

| Added compound | Phase transition temperature (°C.) | Spontaneous polarization nC/cm² |
|---|---|---|
| Compound 10 | SmC* ⇌53⇌ SmA ⇌61⇌ N* ⇌67⇌ Iso | −2.4 |
| Compound 11 | SmC* ⇌53⇌ SmA ⇌61⇌ N* ⇌67⇌ Iso | −4.9 |
| Compound 12 | SmC* ⇌54⇌ SmA ⇌61⇌ N* ⇌67⇌ Iso | −4.8 |
| Compound 13 | SmC* ⇌51⇌ SmA ⇌60⇌ N* ⇌67⇌ Iso | −4.8 |
| Compound 14 | SmC* ⇌51⇌ SmA ⇌56⇌ N* ⇌66⇌ Iso | −8.9 |
| Compound 15 | SmC* ⇌50⇌ SmA ⇌57⇌ N* ⇌65⇌ Iso | −8.4 |
| Compound 16 | SmC* ⇌41⇌ SmA ⇌57⇌ N* ⇌65⇌ Iso | −5.7 |
| Compound 17 | SmC* ⇌49⇌ SmA ⇌57⇌ N* ⇌65⇌ Iso | −9.0 |
| Compound 18 | SmC* ⇌53⇌ SmA ⇌58⇌ N* ⇌66⇌ Iso | −9.1 |
| Compound 19 | SmC* ⇌46.5⇌ SmA ⇌59⇌ N* ⇌65⇌ Iso | −4.2 |
| Compound 20 | SmC* ⇌46⇌ SmA ⇌59⇌ N* ⇌66⇌ Iso | −2.1 |
| Compound 21 | SmC* ⇌52⇌ SmA ⇌58⇌ N* ⇌65⇌ Iso | −7.9 |
| Compound 22 | SmC* ⇌ ⇌ SmA ⇌ ⇌ N* ⇌ ⇌ Iso | −3.6 |
| Compound 23 | SmC* ⇌ ⇌ SmA ⇌ ⇌ N* ⇌ ⇌ Iso | −3.8 |
| Compound 24 | SmC* ⇌ ⇌ SmA ⇌ ⇌ N* ⇌ ⇌ Iso | −2.9 |

We claim:

1. An optically active compound having a δ-valerolactone ring, which is represented by the formula (1):

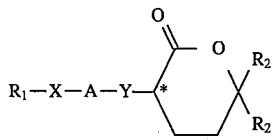

(1)

wherein $R_1$ represents a straight-chain or branched alkyl group having 1 to 18 carbon atoms, a straight-chain or branched alkenyl group having 2 to 18 carbon atoms, a straight-chain or branched alkoxyalkyl group having 1 to 3 carbon atoms in the alkoxy portion and 1 to 18 carbon atoms in the alkyl portion, or any of said groups wherein at least one hydrogen atom is substituted with a halogen, provided that when $R_1$ has a structure capable of having an optically active group, it may be an optically active group or a racemic modification; two $R_2$'s are the same and each represents an alkyl group having 1 to 18 carbon atoms;

X represents a direct bond, —O—,

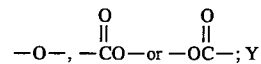

—O—, —CO— or —OC—; Y represents a direct bond,

—CO—,

—O—, —CH$_2$O— or —OCH$_2$—; A represents

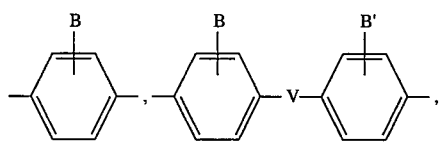

-continued
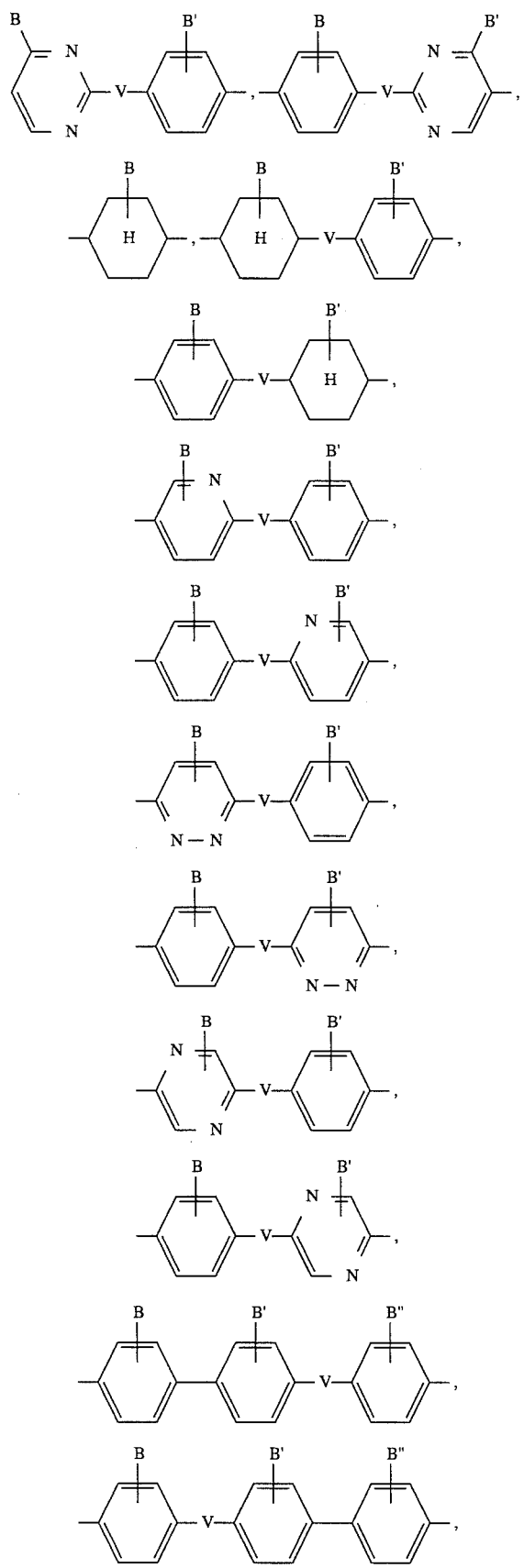
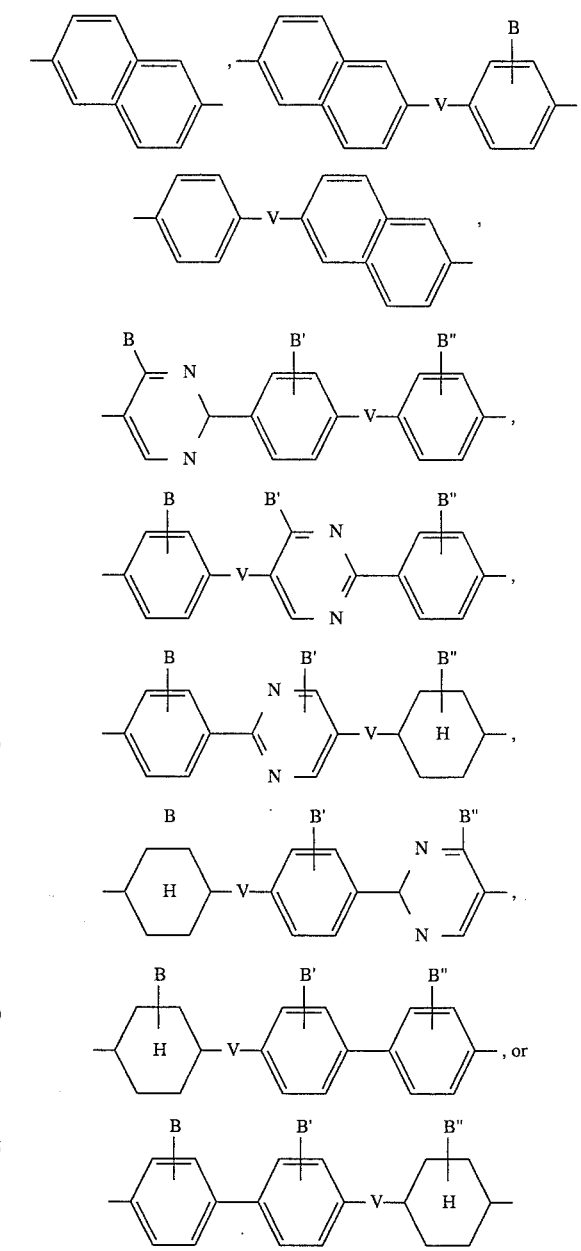
wherein B, B' and B" each independently represent a hydrogen atom, a halogen atom, a cyano group, a methyl group, a methoxy group or a trihalomethyl group and V represents a direct bond, —CH₂O—, —OCH₂—,
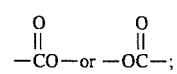
and * represents an asymmetric carbon atom.

2. An optically active compound having a δ-valerolactone ring, which is represented by the formula (2):

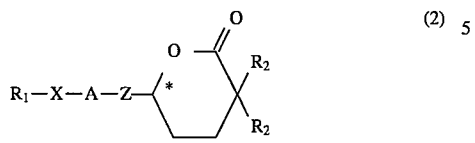 (2)

wherein $R_1$ represents a straight-chain or branched alkyl group having 1 to 18 carbon atoms, a straight-chain or branched alkenyl group having 2 to 18 carbon atoms, a straight-chain or branched alkoxyalkyl group having 1 to 3 carbon atoms in the alkoxy portion and 1 to 18 carbon atoms in the alkyl portion, or any of said groups wherein at least one hydrogen atom is substituted with a halogen, provided that when $R_1$ has a structure capable of having an optically active group, it may be an optically active group or a racemic modification; two $R_2$'s are the same and each represents an alkyl group having 1 to 18 carbon atoms;

X represents a direct bond, —O—,

Z represents a direct bond,

or —OCH$_2$—;

A represents

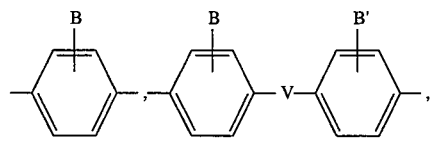

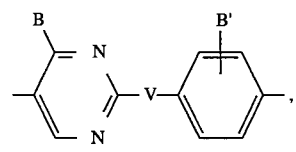

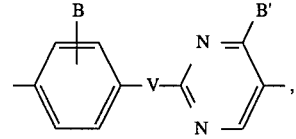

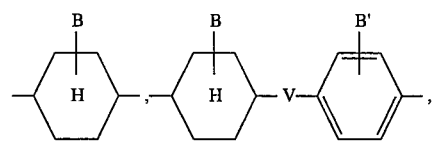

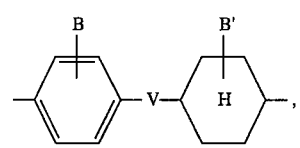

-continued

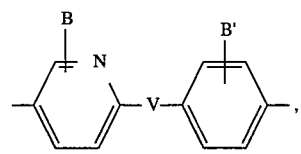

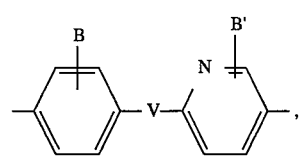

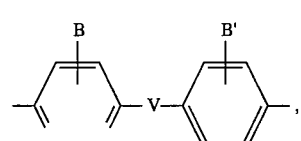

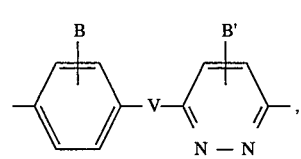

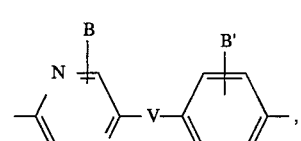

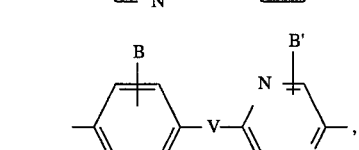

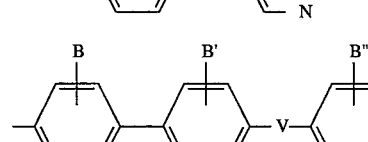

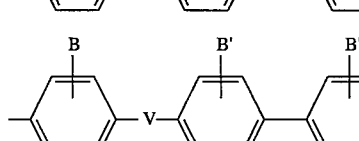

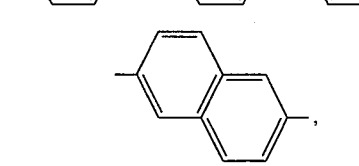

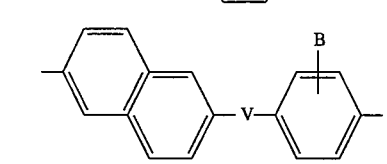

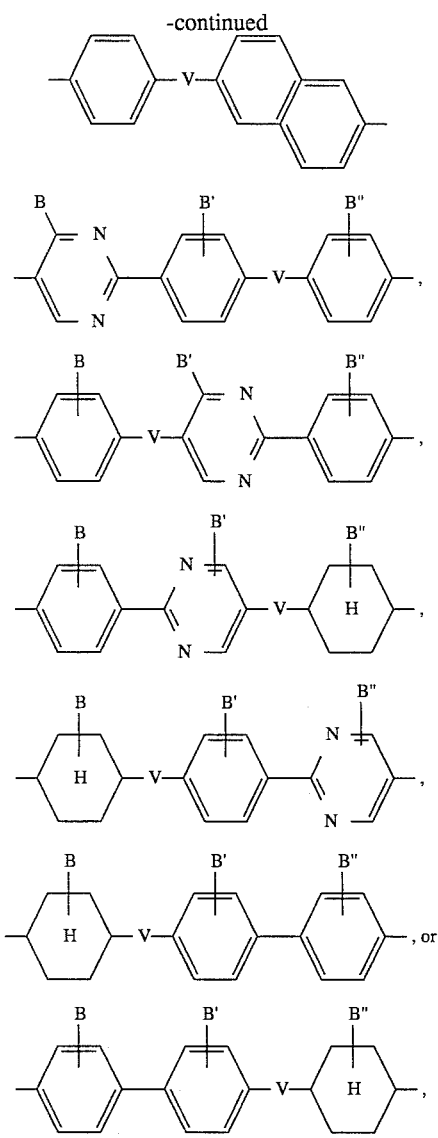

wherein B, B' and B" each independently represent a hydrogen atom, a halogen atom, a cyano group, a methyl group, a methoxy group or a trihalomethyl group and V represents a direct bond, —CH$_2$O—, —OCH$_2$—, $$-\overset{\overset{\displaystyle O}{\|}}{C}O-$$

and * represents an asymmetric carbon atom.

3. An optically active compound of claim 1 wherein R is C$_8$H$_{17}$; X is —O—; A is

[structure: two phenyl rings connected by V, with B and B' substituents]

wherein V is a direct bond and B and B' are hydrogen; Y is $$-\overset{\overset{\displaystyle O}{\|}}{C}-O;$$

and each R$_2$ is —C$_3$H$_7$.

4. An optically active compound of claim 2, wherein R is C$_8$H$_{17}$; X is —O—; A is

[structure: pyrimidine ring connected via V to phenyl ring, with B and B' substituents]

wherein V is a direct bond and B and B' are hydrogen; Y is —OCH$_2$—; and each R$_2$ is C$_2$H$_5$.

5. A liquid crystal composition comprising at least one member selected from the group consisting of optically active compounds according to claim 1.

6. A liquid crystal composition comprising at least one member selected from the group consisting of optically active compounds according to claim 2.

* * * * *

UNITED STATES PATENT AND TRADEMARK OFFICE
CERTIFICATE OF CORRECTION

PATENT NO. : 5,480,580
DATED : January 2, 1996
INVENTOR(S) : Keiichi Sakashita et al.

It is certified that error appears in the above-indentified patent and that said Letters Patent is hereby corrected as shown below:

Claim 2, column 70, lines 2-5, after " O " insert $-\overset{\overset{O}{\|}}{C}O-$ , -- or $-O\overset{\overset{O}{\|}}{C}-$ --.

Signed and Sealed this

Twenty-third Day of July, 1996

Attest:

BRUCE LEHMAN

Attesting Officer     Commissioner of Patents and Trademarks